United States Patent
Salahuddin et al.

(10) Patent No.: US 12,131,748 B2
(45) Date of Patent: Oct. 29, 2024

(54) APPARATUS AND METHOD FOR OPERATING WEARABLE DEVICE

(71) Applicant: SAMSUNG ELECTRONICS CO., LTD., Suwon-si (KR)

(72) Inventors: Md. Salahuddin, Dacca (BD); Anwarul Hoque Mohammad, Dacca (BD); Shyam Akhter Bonny, Dacca (BD); Debashis Maitra, Dacca (BD)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 359 days.

(21) Appl. No.: 17/474,563

(22) Filed: Sep. 14, 2021

(65) Prior Publication Data
US 2021/0407532 A1 Dec. 30, 2021

Related U.S. Application Data

(63) Continuation of application No. PCT/KR2019/004756, filed on Apr. 19, 2019.

(30) Foreign Application Priority Data

Mar. 20, 2019 (KR) .................. 10-2019-0031780

(51) Int. Cl.
*G10L 21/00* (2013.01)
*G10L 15/06* (2013.01)
(Continued)

(52) U.S. Cl.
CPC ........ *G10L 21/0364* (2013.01); *G10L 15/063* (2013.01); *G10L 15/07* (2013.01); *G10L 21/0208* (2013.01)

(58) Field of Classification Search
CPC ... G10L 21/0364; G10L 15/063; G10L 15/07; G10L 21/0208; G10L 17/00; G10L 17/04;
(Continued)

(56) References Cited

U.S. PATENT DOCUMENTS 5,787,187 A 7/1998 Bouchard et al.
6,330,339 B1 12/2001 Ishige et al.
(Continued)

FOREIGN PATENT DOCUMENTS

GB 2531964 A * 5/2016 ............. G10L 15/20
JP 2008028937 A 2/2008
(Continued)

OTHER PUBLICATIONS

"Global $20 Billion Earphones & Headphones Market Outlook and Forecast 2018-2023", Research and Markets: The World's Largest Market Research Store, Jan. 26, 2018, https://www.prnewswire.com/news-releases/global-20-billion-earphones--headphones-market-outlook-and-forecast-2018-2023-300588744.html 4 pages.
(Continued)

*Primary Examiner* — Douglas Godbold
*Assistant Examiner* — Parker Mayfield
(74) *Attorney, Agent, or Firm* — Sughrue Mion, PLLC

(57) ABSTRACT

A wearable device and a method of operating the wearable device are provided. The wearable device includes: a memory configured to store one or more instructions; and at least one processor configured to execute the one or more instructions to: receive, as an input, a surrounding sound of surroundings of the wearable device: determine an operation mode from among a plurality of operation modes, based on the received input; and perform a preset operation according to the determined operation mode.

13 Claims, 16 Drawing Sheets

(51) Int. Cl.
    *G10L 15/07*     (2013.01)
    *G10L 21/0208*   (2013.01)
    *G10L 21/0364*   (2013.01)

(58) Field of Classification Search
    CPC ..... G10L 21/0316; G10L 25/51; G10L 25/78;
        G10L 17/22; A61B 5/7267; A61B 5/6803;
        A61B 5/7203; A61B 5/4812; A61B
        5/374; A61B 2560/0209; A61B 5/372;
        G06F 1/16; G06F 3/16; G06F 1/163;
        G06F 3/015; G06F 2203/011; H04R
        2499/11
    See application file for complete search history.

(56) References Cited

U.S. PATENT DOCUMENTS

| | | | |
|---|---|---|---|
| 8,285,208 B2* | 10/2012 | Terlizzi | H04M 1/05 379/433.03 |
| 9,324,322 B1* | 4/2016 | Torok | H04R 3/02 |
| 9,497,530 B1 | 11/2016 | Campbell et al. | |
| 9,711,127 B2 | 7/2017 | Hui et al. | |
| 9,716,939 B2* | 7/2017 | Di Censo | H04R 1/1083 |
| 9,913,037 B2 | 3/2018 | Suzuki et al. | |
| 9,961,444 B2* | 5/2018 | Ichimura | H04R 1/1083 |
| 10,178,482 B2 | 1/2019 | Yang et al. | |
| 10,659,898 B2 | 5/2020 | Lyren et al. | |
| 10,664,228 B1* | 5/2020 | Senapati | H04N 21/42204 |
| 10,937,445 B2 | 3/2021 | Atkinson | |
| 2006/0155389 A1 | 7/2006 | Pessolano et al. | |
| 2009/0249478 A1 | 10/2009 | Rosener et al. | |
| 2010/0022283 A1 | 1/2010 | Terlizzi | |
| 2015/0222977 A1* | 8/2015 | Angel, Jr. | H04R 1/105 381/74 |
| 2016/0173049 A1* | 6/2016 | Mehta | H03G 3/32 381/57 |
| 2016/0277858 A1* | 9/2016 | Gelter | G06F 16/683 |
| 2017/0215742 A1 | 8/2017 | Wisbey et al. | |
| 2018/0167715 A1* | 6/2018 | Graylin | G06F 3/165 |
| 2018/0233125 A1* | 8/2018 | Mitchell | G10L 25/78 |
| 2019/0028803 A1* | 1/2019 | Benattar | H04S 7/304 |
| 2020/0265823 A1* | 8/2020 | Kremer | G10K 11/178 |
| 2020/0296521 A1* | 9/2020 | Wexler | G06F 3/167 |

FOREIGN PATENT DOCUMENTS

| | | |
|---|---|---|
| JP | 2016127376 A | 7/2016 |
| JP | 2016139944 A | 8/2016 |
| KR | 1020070009823 A | 1/2007 |
| KR | 101535112 B1 | 7/2015 |
| KR | 1020160111744 A | 9/2016 |
| WO | 2010140976 A2 | 12/2010 |

OTHER PUBLICATIONS

"8 Wireless Earbuds That Are Way Better Than Apple's Airpods", Highsnobiety, https://www.highsnobiety.com/2016/11/15/best-wireless-earbuds/ Nov. 15, 2016, 13 pages.
"Gartner Says Worldwide Wearable Device Sales to Grow 17 Percent in 2017", Newsroom, Eghan, UK, Aug. 24, 2017, https://www.gartner.com/newsroom/id/3790965 5 pages.
"Highest-selling wearable will continue to be Bluetooth audio devices: Gartner", ZDNet, Aug. 24, 2017, http://www.zdnet.com/article/highest-selling-wearable-will-continue-to-be-bluetoothaudio-devices-gartner/ 4 pages.
"Road traffic injuries", World Health Organization, Jun. 21, 2021, http://www.who.int/mediacentre/factsheets/fs358/en/ 6 pages.
Goverdovsky, V., et al., "In-ear EEG from viscoelastic generic earpieces: Robust and unobtrusive 24/7 monitoring", IEEE Sensors Journal, 2014, In-Ear EEG: https://ieeexplore.IEEE.org/document/7217787/?tp=&arnumber=7217787 pp. 1-7.
Singh, N., et al., "Robust Voice Activity Detection Algorithm based on Long Term Dominant Frequency and Spectral Flatness Measure", I.J. Image, Graphics and Signal Processing, 2017, vol. 8, http://www.mecs-press.org/ijigsp/ijigsp-v9-n8/IJIGSP-V9-N8-6.pdf pp. 50-58.
Sarvade, S., et al., "Speech Enhancement Using Spectral Flatness Measure Based Spectral Subtraction", IOSR Journal of VLSI and Signal Processing, vol. 7, Issue 2, Ver. 1, Mar.-Apr. 2017, http://www.iosrjournals.org/iosr-jvlsi/papers/vol7-issue2/Version-1/F0702014146.pdf pp. 41-46.
Isik, Y., et al., "Single-Vhannel Multi-Speaker Separation using Deep Clustering", Mitsubishi Electric Research Laboratories, Sep. 2016, http://cn.arxiv.org/pdf/1607.02173 7 pages.
Martin, A., et al., "Speaker Recognition in a Multi-Speaker Environment", http://www.imm.dtu.dk/~lfen/Speaker%20Recognition%20in%20a%20Multi-Speaker%20Environment.pdf Sep. 1, 2001, 4 pages.
Scholl, P., et al., "A Feasibility Study of Wrist-Worn Accelerometer Based Detection of Smoking Habits", Technische Universität Darmstadt, Jul. 4, 2012, 6 pages.
Parate, A., et al., "Detecting Eating and Smoking Behaviors Using Smartwatches", Mobile Health, 2017, pp. 175-201.
Tang, Q., "Automated Detection of Puffing and Smoking with Wrist Accelerometers", Northeastern University, Aug. 2014, pp. 1-34 (39 pages).
Haskins, B., et al., "A systematic review of smartphone applications for smoking cessation", Systematic Reviews, May 2017, pp. 292-299 (9 pages).
Imtiaz, M., et al., "Development of a Multisensory Wearable System for Monitoring Cigarette Smoking Behavior in Free-Living Conditions", Electronics, 2017, vol. 6, No. 104, pp. 1-21 (22 pages).
Davarci, E., et al., " Age Group Detection Using Smartphone Motion Sensors", 2017 25th European Signal Processing Conference, pp. 2265-2269.
Mayo, B., "Significant AAPL investors put pressure on Apple to add better parental control features to iPhones and iPads", 9to5Mac, Jan. 8, 2018, https://9to5mac.com/2018/01/08/parental-control-features-iphone-ipad/ 4 pages.
Palladino, V., "The Kids Aren't All Right—Apple planning new, "robust" parental controls to help protect children, teens", Jan. 9, 2018, arsTEC, https://arstechnica.com/gadgets/ . . . /apple-will-introduce-more-robust-parental-controls/ 3 pages.
"Online Safety for Children & Families—Google Safety Center", Nov. 12, 2012, https://www.google.com/safetycenter/families/start/ pp. 1-7.
International Search Report (PCT/ISA/210) dated Dec. 20, 2019 issued by the International Searching Authority in International Application No. PCT/KR2019/004756.
Communication dated Mar. 28, 2024, issued by the Korean Patent Office in Korean Application No. 10-2019-0031780.

* cited by examiner

APPARATUS AND METHOD FOR OPERATING WEARABLE DEVICE

CROSS-REFERENCE TO RELATED APPLICATIONS

This application is a continuation of International Application No. PCT/KR2019/004756 filed on Apr. 19, 2019, and claims priority from Korean Patent Application No. 2019-0031780 filed on Mar. 20, 2019, the disclosure of which is incorporated herein in its entirety by reference.

BACKGROUND

1. Field

The disclosure relates to an apparatus and method of operating a wearable device.

2. Description of Related Art

Recently, as users' demands for earphones and headphones among wearable devices that can be worn on a user's body increase, various types of earphones and headphones have been developed. Accordingly, various demands for functions of earphones and headphones are being made, besides a traditional function of providing a user of a wearable device with a sound of an audio of a content reproduced by another electronic device by using electronic devices such as earphones and headphones.

SUMMARY

Provided is a wearable device and a method of operating the wearable device.

Provided is also a wearable device and a method of receiving a surrounding sound of surroundings of the wearable device as an input and determining an operation mode of the wearable device, based on the received input.

Provided is also a wearable device and a method of performing a preset operation according to a determined operation mode.

Provided is also a wearable device and a method of determining an operation mode of the wearable device by using artificial intelligence (AI) technology or performing a preset operation.

According to an embodiment, a method of operating a wearable device may include: receiving, as an input, a surrounding sound of the wearable device, determining an operation mode from among a plurality of operation modes, based on the received input, and performing a preset operation according to the determined operation mode.

According to an embodiment, a wearable device may include: a memory configured to store one or more instructions: and at least one processor configured to execute the one or more instructions to receive, as an input, a surrounding sound of the wearable device, determine an operation mode from among a plurality of operation modes, based on the received input, and perform a preset operation according to the predetermined operation mode.

According to an embodiment, the plurality of operation modes may include at least one of: a conversation mode representing a conversation state between a user of the wearable device and a speaker; an announcement mode representing detection of an announcement from an external sound source; and a power control mode for controlling power consumption of the wearable device.

According to an embodiment, the at least one processor may execute the one or more instructions to determine the conversation mode to be the operation mode of the wearable device, based on determining that a voice signature detected from the received input matches with a pre-stored voice signature.

According to an embodiment, the at least one processor may execute the one or more instructions to determine the announcement mode to be the operation mode of the wearable device, based on determining that an announcement signature is detected from the received input.

According to an embodiment, the at least one processor may be configured to execute the one or more instructions to determine the power control mode to be the operation mode of the wearable device, based on determining that a magnitude of the received input is less than a threshold.

According to an embodiment, based on determining that the conversation mode to be the operation mode of the wearable device operates, the preset operation may include at least one of: canceling noise from the received input; adjusting a volume of an audio of a content reproduced by the wearable device; and amplifying a voice of the speaker.

DESCRIPTION OF EMBODIMENTS

Figure 1:
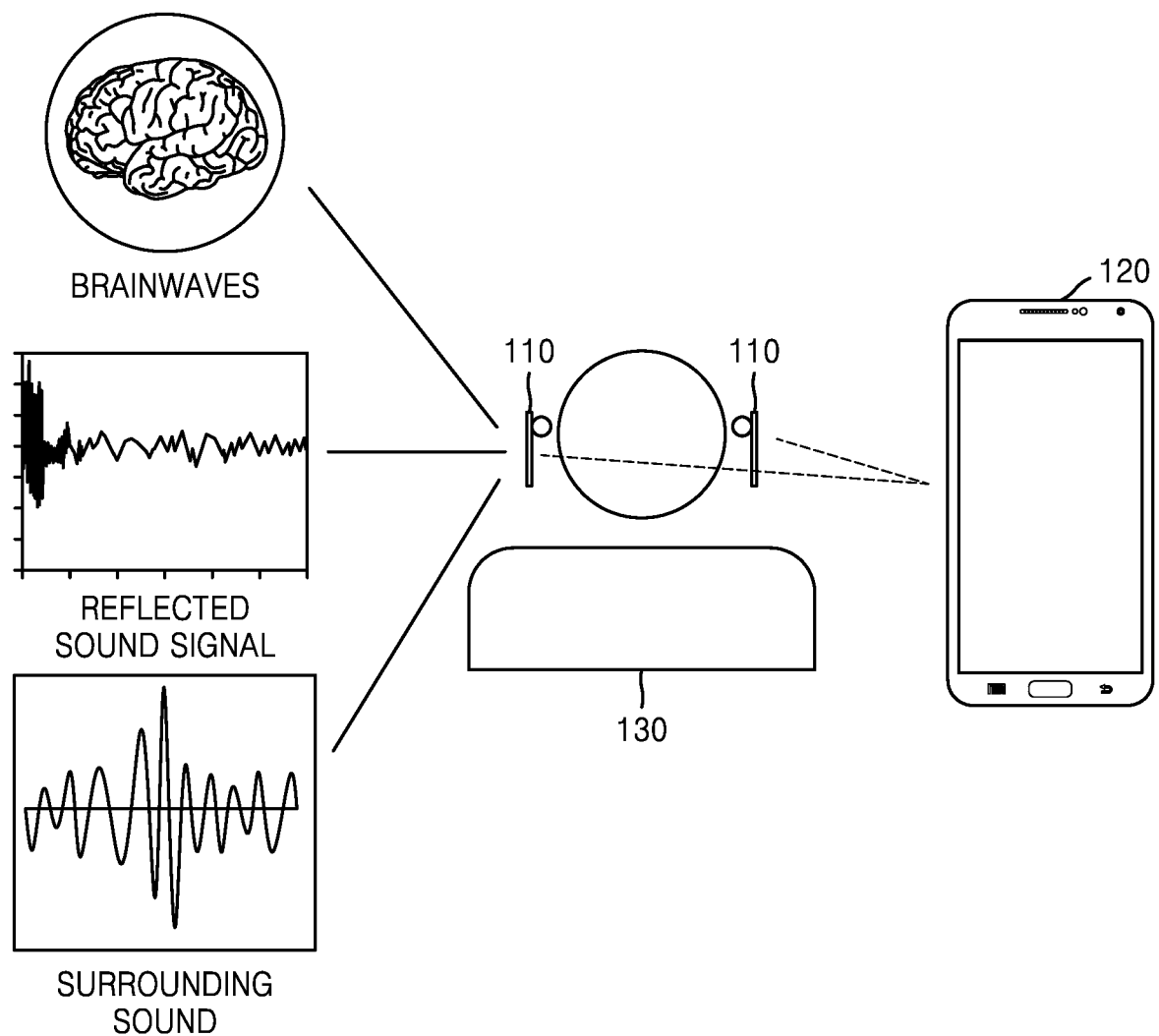
FIG. 1 is a conceptual view of an operation of a wearable device, according to an embodiment of the disclosure.

Embodiments of the disclosure will now be described more fully with reference to the accompanying drawings such that one of ordinary skill in the art to which the disclosure pertains may easily execute the disclosure. The disclosure may, however, be embodied in many different forms and should not be construed as being limited to the embodiments set forth herein. In the drawings, parts irrelevant to the description are omitted for the simplicity of explanation, and like numbers refer to like elements throughout.

Although general terms widely used at present were selected for describing the disclosure in consideration of the functions thereof, these general terms may vary according to intentions of one of ordinary skill in the art, case precedents, the advent of new technologies, or the like. Hence, the terms must be defined based on their meanings and the contents of the entire specification, not by simply stating the terms.

While such terms as "first", "second", etc may be used to describe various components, such components must not be limited to the above terms. The above terms are used to distinguish one component from another.

Throughout the specification, when an element is referred to as being "connected" or "coupled" to another element, it can be directly connected or coupled to the other element, or can be electrically connected or coupled to the other element with intervening elements interposed therebetween. The terms "comprises" and/or "comprising" or "includes" and/or "including" when used in this specification, specify the presence of stated elements, but do not preclude the presence or addition of one or more other elements.

Phrases such as "in an embodiment" appearing in various places in this disclosure do not necessarily all refer to the same embodiment.

An embodiment of the disclosure may be represented by functional block configurations and various processing operations. Some or all of these functional blocks may be implemented using various numbers of hardware and/or software configurations that perform specific functions. For example, the functional blocks of the disclosure may be implemented by one or more microprocessors, or by circuit configurations for a certain function. For example, the functional blocks of the disclosure may be implemented in various programming or scripting languages. The functional blocks may be implemented as an algorithm running on one or more processors. The disclosure may employ the conventional art for electronic configuration, signal processing, and/or data processing, for example. Terms such as "mechanism", "element", "means", and "configuration" may be used broadly and are not limited to mechanical and physical configurations.

In addition, connecting lines or connecting members between the components shown in the drawings only exemplify functional connections and/or physical or circuit connections. In an actual device, a connection between components may be represented by various functional connections, physical connections, or circuit connections that are replaceable or added.

The disclosure will now be described more fully with reference to the accompanying drawings.

FIG. 1 is a conceptual view of an operation of a wearable device, according to an embodiment of the disclosure.

Referring to FIG. 1, a user 130 may hear a sound or audio (interchangeably used herein) of a content reproduced by a user terminal 120 through a wearable device 110. For example, the wearable device 110 may include an audio device such as an earphone and a headphone. According to an embodiment, the wearable device 110 may be connected to the user terminal 120 or another electronic device wirelessly or by wire. Here, the user terminal 120 may represent a portable device such as a cellphone, a notebook computer, a tablet, etc., not being limited thereto. According to an embodiment, the wearable device 110 may be wirelessly connected to the user terminal 120 or another electronic device by using Bluetooth™, Bluetooth Low Energy (BLE), Ultra WideBand (UWB), or Wi-Fi™. For example, the wearable device 110 may receive a surrounding sound of the wearable device 110. Examples of the surrounding sound of the wearable device 110 may include a voice of the user 130, a voice of a speaker who the user 130 is talking with, a voice of another speaker who the user 130 is not talking with, and a person's voice that comes out of a loudspeaker.

According to an embodiment, the wearable device 110 may receive the surrounding sound of the wearable device 110 as an input, and may determine an operation mode of the wearable device 110. Examples of the operation mode may include a conversation mode representing a conversation state between a user and a speaker, an announcement mode representing detection of an announcement that is output from an external sound source, and a power control mode for controlling power consumption of the wearable device 110. Herein, the speaker may include a speaker speaking to the user through the user terminal 120 or outside the user terminal 120, and the external sound source may include a device other than the user terminal 120.

According to an embodiment, the wearable device 110 may receive a reflected sound signal. For example, the wearable device 110 may output a sound signal and receive a reflected sound signal obtained by reflecting the output sound signal in the ears of the user 130. The above-described technique of outputting the sound signal and receiving the reflected sound signal may be included in acoustic reflectometry, According to an embodiment, the wearable device 110 may analyze an ear state of the user 130 wearing the wearable device 110 by using acoustic reflectometry. For example, the wearable device 110 may detect a disease such as middle ear infection of the ears of the user 130 by using acoustic reflectometry.

According to an embodiment, the wearable device 110 may receive brainwaves of the user 130. The wearable device 110 may include an electroencephalography (EEG) sensor. The wearable device 110 may receive brainwaves from the brain of the user 130 by using the EEG sensor. By analyzing the received brainwaves, the wearable device 110 may determine a sleep state of the user 130, measure a sleep quality of the user 130, or determine a stress level of the user 130. Examples of the sleep state of the user may include an awake state, a rapid eye movement (REM) sleep state representing a shallow sleep close to the awake state, and a non-REM sleep state representing a deeper sleep than the REM sleep. As described above, the wearable device 110 may receive various inputs, and may perform an operation corresponding to each of the received various inputs.

Figure 2:
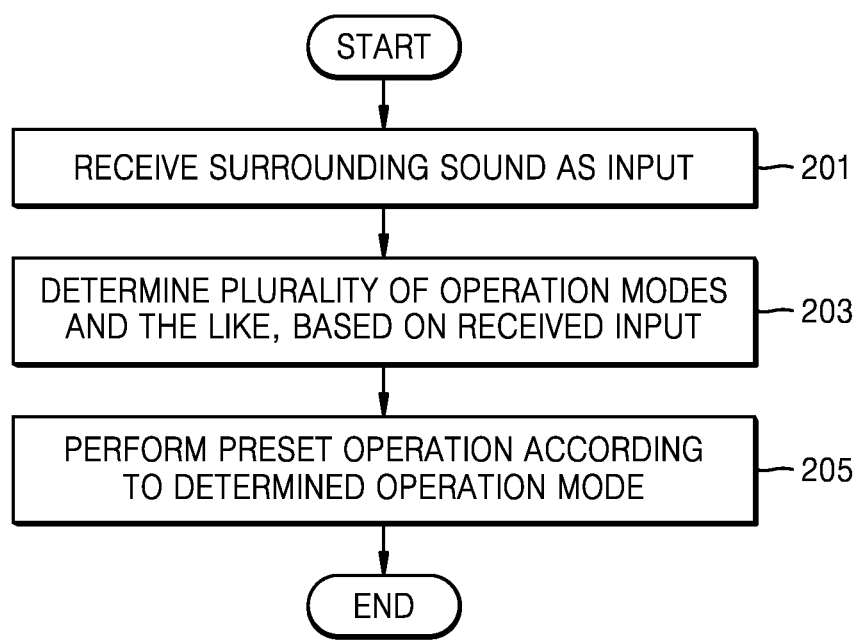
FIG. 2 is a flowchart of a method of operating a wearable device, according to an embodiment of the disclosure.

FIG. 2 is a flowchart of a method of operating a wearable device, according to an embodiment of the disclosure.

Referring to FIG. 2, in operation 201, the wearable device 110 may receive a surrounding sound as an input. Examples of the surrounding sound of the wearable device 110 may include a voice of the user 130, a voice of a speaker who the user 130 is talking with, a voice of another speaker who the user 130 is not talking with, and a person's voice that comes out of a loudspeaker. According to an embodiment, the input received by the wearable device 110 may include a voice signature or an announcement signature. According to an embodiment, the voice signature may be an identifier representing a unique voice of each person. Thus, the voice signature may be different for each person. According to an embodiment, the announcement signature may be an identifier representing a broadcasting signal output by a loudspeaker of a public facility such as a bus stop, a subway station, or a train station.

In operation 203, the wearable device 110 may determine a plurality of operation modes and the like, based on the received input. According to an embodiment, the plurality of operation modes may include a conversation mode representing a conversation state between a user of the wearable device 110 and a speaker, an announcement mode representing detection of an announcement from an external sound source, and a power control mode for controlling power consumption of the wearable device 110. According to an embodiment, when the voice signature detected from the received input matches with a pre-stored voice signature, the wearable device 110 may determine the conversation mode from among the plurality of operation modes as the operation mode, and may update the pre-stored voice signature, based on the detected voice signature. According to an embodiment, when an announcement signature is detected from the received input, the wearable device 110 may determine the announcement mode from among the plurality of operation modes as the operation mode. According to an embodiment, when the magnitude of the received input is less than a threshold, the wearable device 110 may determine the power control mode from among the plurality of operation modes as the operation mode. According to an embodiment, the threshold refers to the magnitude of a sound expressed as a decibel (dB).

In operation 205, the wearable device 110 may perform a preset operation according to the determined operation mode. In other words, the wearable device 110 may determine the conversation mode, the announcement mode, or the power control mode as the operation mode, and may perform an operation corresponding to the determined operation mode. According to an embodiment, when the wearable device 110 operates in the conversation mode, the wearable device 110 may perform at least one of an operation of canceling noise from the received input, an operation of adjusting a volume of a content reproduced by the wearable device 110 including stopping reproduction of an audio of the content, and an operation of amplifying the voice of a speaker who talks with the user 130 of the wearable device 110.

According to an embodiment, when the wearable device 110 operates in the announcement mode, the wearable device 110 may perform at least one of an operation of canceling noise from the received input, and an operation of adjusting a volume of a content reproduced by the wearable device 110 including stopping reproduction of an audio of the content. According to an embodiment, when the wearable device 110 operates in the power control mode, the wearable device 110 may perform an operation of adjusting a sampling speed of an input or an operation of deactivating noise cancellation. As described above with reference to FIG. 2, the wearable device 110 may determine the operation mode of the wearable device 110, and may perform an operation corresponding to the determined operation mode.

Figure 3:
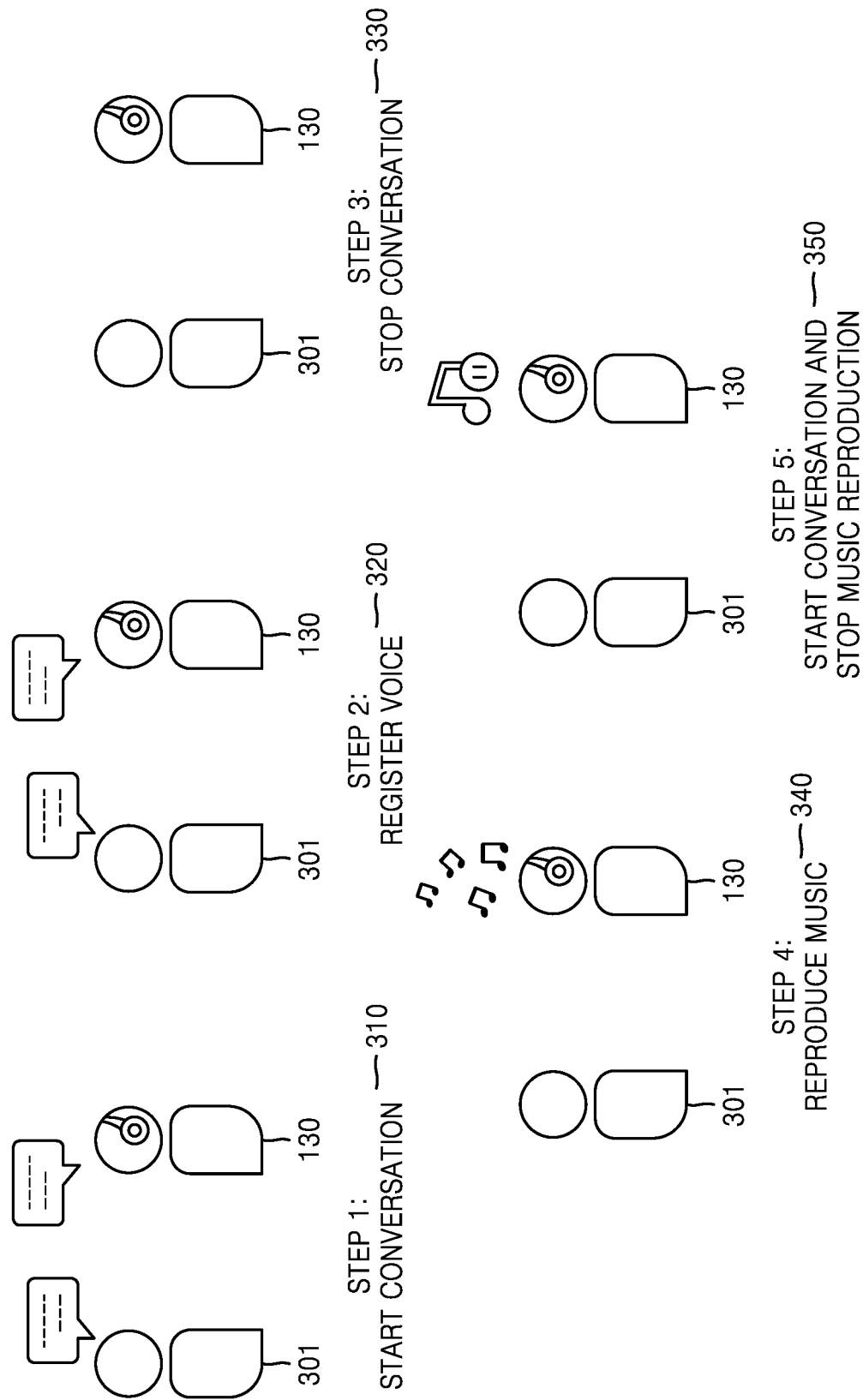
FIG. 3 illustrates an operation of a wearable device in a conversation state, according to an embodiment of the disclosure.

FIG. 3 illustrates an operation of a wearable device in a conversation state, according to an embodiment of the disclosure.

Referring to FIG. 3, in step 1 (310), the user 130 of the wearable device 110 and a speaker 301 may start a conversation. According to an embodiment, the voice of the user 130 may be defined as a first voice, and the voice of the speaker may be defined as a second voice. The wearable device 110 may receive the first voice from the user, and may receive the second voice from the speaker.

In step 2 (320), the wearable device 110 may register a voice. For example, after conversation between the user 130 and the speaker 301 starts, the wearable device 110 may apply a priority to the second voice received from the speaker 301, and may register the second voice in the wearable device 110. For example, the wearable device 110 may store the second voice at a high priority or a low priority. According to an embodiment, the wearable device 110 may store the registered second voice in a storage of the wearable device 110, store the registered second voice in a storage of the user terminal 120 connected to the wearable device 110 in a wired or wireless manner, or store the registered second voice in another storage. According to an embodiment, the wearable device 110 may also register and store the voice of a person other than the speaker 301. According to an embodiment, the wearable device 110 may register a voice from a surrounding sound multiple times.

In step 3 (330), the user 130 of the wearable device 110 and the speaker 301 may stop the conversation. According to an embodiment, when the first voice of the user 130 or the second voice of the speaker 301 is not detected, the wearable device 110 may determine that the conversation between the user 130 and the speaker 301 has stopped. Step 3 (330) is not essential and may be omitted.

In step 4 (340), the user 130 of the wearable device 110 may reproduce an audio of a content such as music. In other words, the user 130 of the wearable device 110 may reproduce the audio of the content by using the user terminal 120, and may listen to the reproduced audio of the content through the wearable device 110.

In step 5 (350), the user 130 of the wearable device 110 and the speaker 301 may start a conversation, and the reproduction of the audio of the content by the wearable device 110 may be stopped. For example, when the speaker 301 speaks again while the user 130 is listening to the reproduced audio of the content through the wearable device 110, the wearable device 110 may detect the second voice of the speaker 301, and may ascertain that the detected second voice is a voice pre-registered in the wearable device 110. When the second voice is a voice pre-registered in the wearable device 110, the wearable device 110 may stop the reproduction of the audio of the content so that the second voice of the speaker 301 is heard by the user 130. As described above, when the user 130 of the wearable device 110 and the speaker 301 have a conversation, the wearable device 110 may recognize the voice of the user 130 or the speaker 301, and may perform an operation such as content playback stoppage or content volume adjustment.

Figure 4:
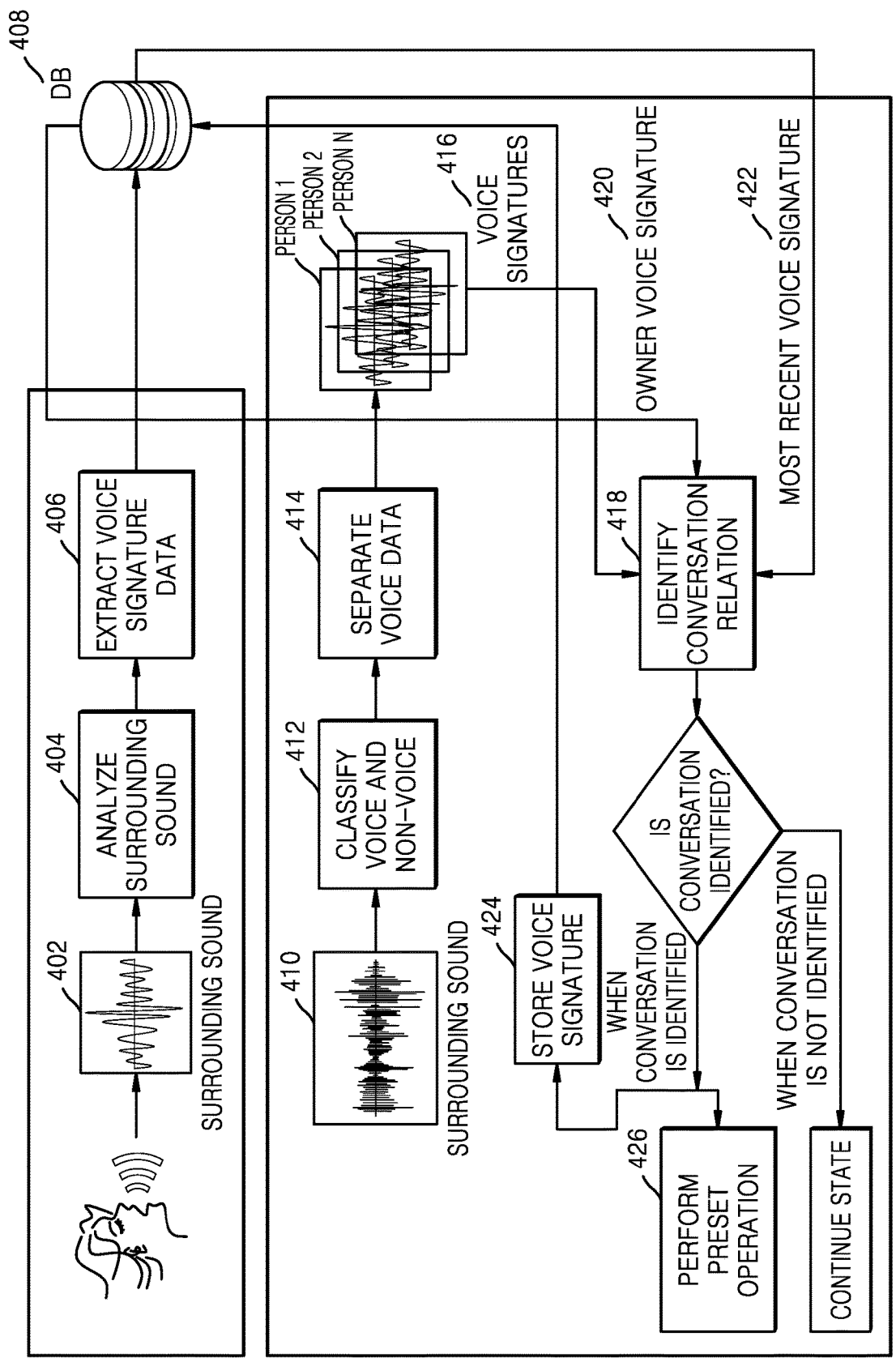
FIG. 4 is a schematic diagram of an overall procedure in which a wearable device operates when an operation mode of the wearable device is a conversation mode, according to an embodiment of the disclosure.

FIG. 4 is a schematic diagram of an overall procedure in which a wearable device operates when an operation mode of the wearable device is a conversation mode, according to an embodiment of the disclosure.

Referring to FIG. 4, the wearable device 110 may identify the voice of the user 130 of the wearable device 110. For example, the wearable device 110 may receive a surrounding sound 402. The wearable device 110 may analyze the received surrounding sound 402 (operation 404). The wearable device 110 may extract voice signature data from the received surrounding sound 402 (operation 406). For example, the wearable device 110 may extract a voice signature representing the voice of the user 130 from the received surrounding sound 402. The wearable device 110 may store the extracted voice signature data in a database (DB) 408. According to an embodiment, the DB 408 may be included in the wearable device 110, may be included in the terminal 120 connected to the wearable device 110 in a wired or wireless manner, or may be included in another storage. The above-described process in which the voice of the user 130 of the wearable device 110 is identified may be referred to as an owner identification process.

When the operation mode of the wearable device 110 is the conversation mode, smart noise cancellation may be performed. For example, the wearable device 110 may receive a surrounding sound 410. The wearable device 110 may classify a voice and a non-voice from the received surrounding sound 410 (operation 412). For example, the voice may refer to the voice of the user 130 or another speaker, and each voice may include a voice signature. The non-voice may refer to a sound including no voice signatures. The wearable device 110 may separate voice data (operation 414). For example, the wearable device 110 may separate voice data of one or more persons from the voice classified from the surrounding sound 410.

According to an embodiment, the voice data may include a voice signature. The wearable device 110 may identify a conversation relation, based on separated voice signatures 416, an owner voice signature 420, or a most recent voice signature 422 (operation 418). For example, when at least one of the voice signatures 416 matches with a voice signature pre-stored in the DB 408, the wearable device 110 may identify the conversation relation. In other words, the wearable device 110 may identify that the user 110 and the speaker are in a conversation state. The wearable device 110 may also identify which speaker the user 110 is in a conversation with, via voice signature matching. In more detail, when at least one of the voice signatures 416 matches with the most recent voice signature 422 stored in the DB 408, the wearable device 110 may identify the conversation relation.

According to an embodiment, the separated voice signatures may include voice signatures corresponding to person 1, person 2, through person N. According to an embodiment, the owner voice signature 420 may refer to a voice signature representing the voice of the user of the wearable device 110. The owner voice signature 420 may be stored in the DB 408. According to an embodiment, the most recent voice signature 422 may refer to a voice signature most recently stored in the DB 408 after identifying the conversation relation.

When a conversation is not identified, namely, when the wearable device 110 does not identify a conversation relation between the user 130 and the speaker, a state where the wearable device 110 performs operations 410, 412, 414 and 418 again may continue. When a conversation is identified, namely, when the wearable device 110 identifies a conversation relation between the user 130 and the speaker, the wearable device 110 may store a voice signature (operation 424). For example, the wearable device 110 may store a voice signature detected for conversation relation identification from among the voice signatures 416 in the DB 408, and may update a pre-stored voice signature, based on the detected voice signature.

When the conversation is identified, the wearable device 110 may perform a preset operation (operation 426). For example, the wearable device 110 may perform at least one operation of canceling noise from an input received by the wearable device 110, amplifying a voice of a speaker in a conversation relation with the user 130, or adjusting the volume of content reproduced by the wearable device 110 so that the user 130 may hear the voice of the speaker. Operation 424 may be performed before or after operation 426, or in any other stage. As described above, the wearable device 110 may identify a conversation state between the user 130 and the speaker, and may perform a preset operation such as noise cancellation. An operation of the wearable device 110 when the operation mode of the wearable device 110 is the conversation mode will now be described in more detail with reference to FIGS. 5 through 9.

Figure 5:
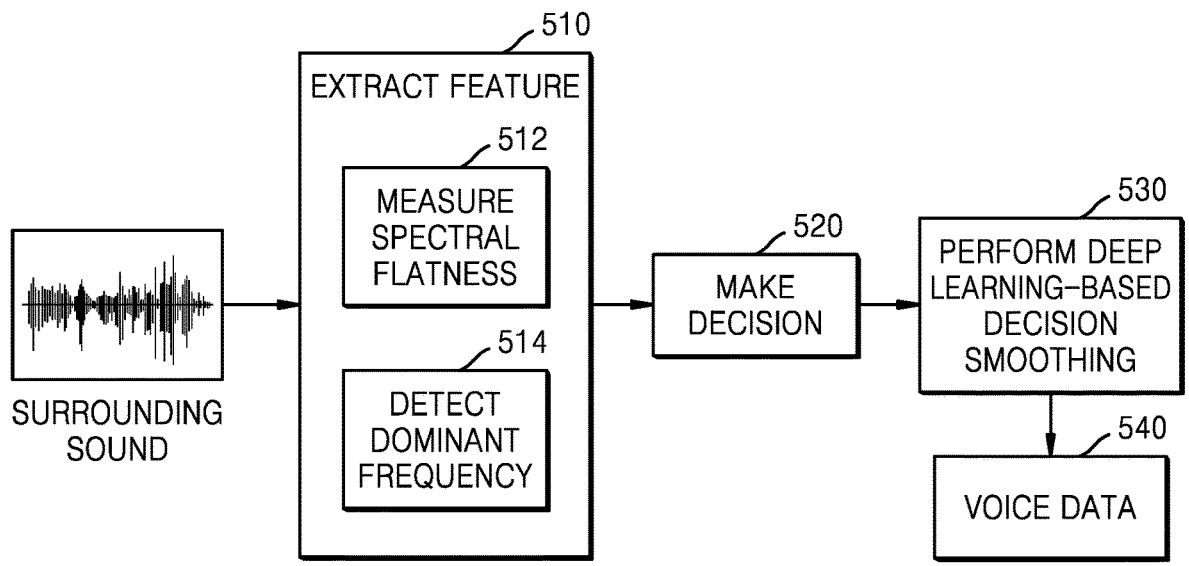
FIG. 5 is a schematic diagram of voice and non-voice classification by a wearable device, according to an embodiment of the disclosure.

FIG. 5 is a schematic diagram of voice and non-voice classification by a wearable device, according to an embodiment of the disclosure.

Referring to FIG. 5, the wearable device 110 may receive a surrounding sound. The wearable device 110 may extract a feature from the received surrounding sound (operation 510). For example, the wearable device 110 may measure spectral flatness of the received surrounding sound (operation 512), and/or may detect a dominant frequency (operation 514). According to an embodiment, the spectral flatness may refer to a value that is measured to characterize an audio spectrum during digital signal processing. The spectral flatness may be measured in a unit of decibel (dB). According to an embodiment, the dominant frequency may refer to a frequency that transmits largest energy from among frequencies on a frequency spectrum. For example, the dominant frequency may refer to a frequency having a largest amplitude. The wearable device 110 may extract a feature from the received surrounding sound (operation 510) by measuring the spectral flatness of the received surrounding sound (operation 512) and/or detecting the dominant frequency (operation 514).

The wearable device 110 may make a decision by using the extracted feature of the surrounding sound (operation 520). For example, the wearable device 110 may determine existence of a voice signal, based on the extracted spectral flatness and/or the extracted dominant frequency of the surrounding sound. According to an embodiment, after determining existence of the voice signal, the wearable device 110 may perform deep learning-based decision smoothing (operation 530). For example, the wearable device 110 may determine existence or absence of the voice signal from the surrounding sound by using AI technology, and may correct the determination. When the wearable device 110 determines from the extracted feature that no voice signals exist, but a voice signal is detected later from the surrounding sound via AI technology, the decision made by the wearable device 110 may be corrected to a decision that a voice signal exists.

After the above-described feature extraction from the surrounding sound, the above-described decision making, and the above-described decision correction, the wearable device 110 may classify voice and non-voice signals from the surrounding sound, and may extract voice data 540. According to an embodiment, the above-described feature extraction, the above-described decision making, and the above-described deep learning based decision smoothing may be performed by the wearable device 110 or the user terminal 120.

Figure 6:
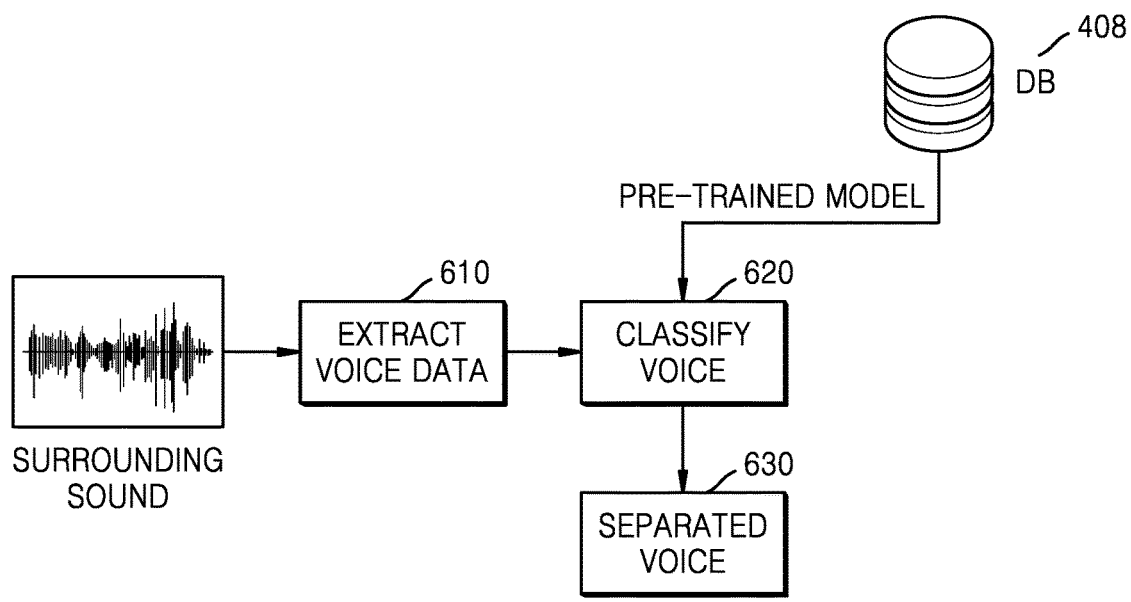
FIG. 6 is a schematic diagram of voice data separation by a wearable device, according to an embodiment of the disclosure.

FIG. 6 is a schematic diagram of voice data separation by a wearable device, according to an embodiment of the disclosure.

Referring to FIG. 6, the wearable device 110 may extract voice data from the surrounding sound (operation 610). For example, the wearable device 110 may classify a voice and a non-voice from the surrounding sound by using the method described above with reference to FIG. 5, and may extract the voice data. The wearable device 110 may classify a voice from the extracted voice data (operation 620). For example, the wearable device 110 may identify voice signatures of a plurality of speakers from the voice data, and may classify a voice of each speaker.

According to an embodiment, the wearable device 110 may classify a voice by using a pre-trained model in the DB 408. For example, a voice signature corresponding to each speaker may be pre-stored in the DB 408, and the wearable device 110 may classify a voice of each speaker from the extracted voice data by using information about the pre-stored voice signatures. The wearable device 110 may obtain a separated voice 630 through the voice classification. Through the above-described voice data extraction and the above-described voice classification, the wearable device 110 may obtain a separated voice of each speaker. According to an embodiment, the above-described voice data extraction and the above-described voice classification may be performed by the wearable device 110 or the user terminal 120.

Figure 7:
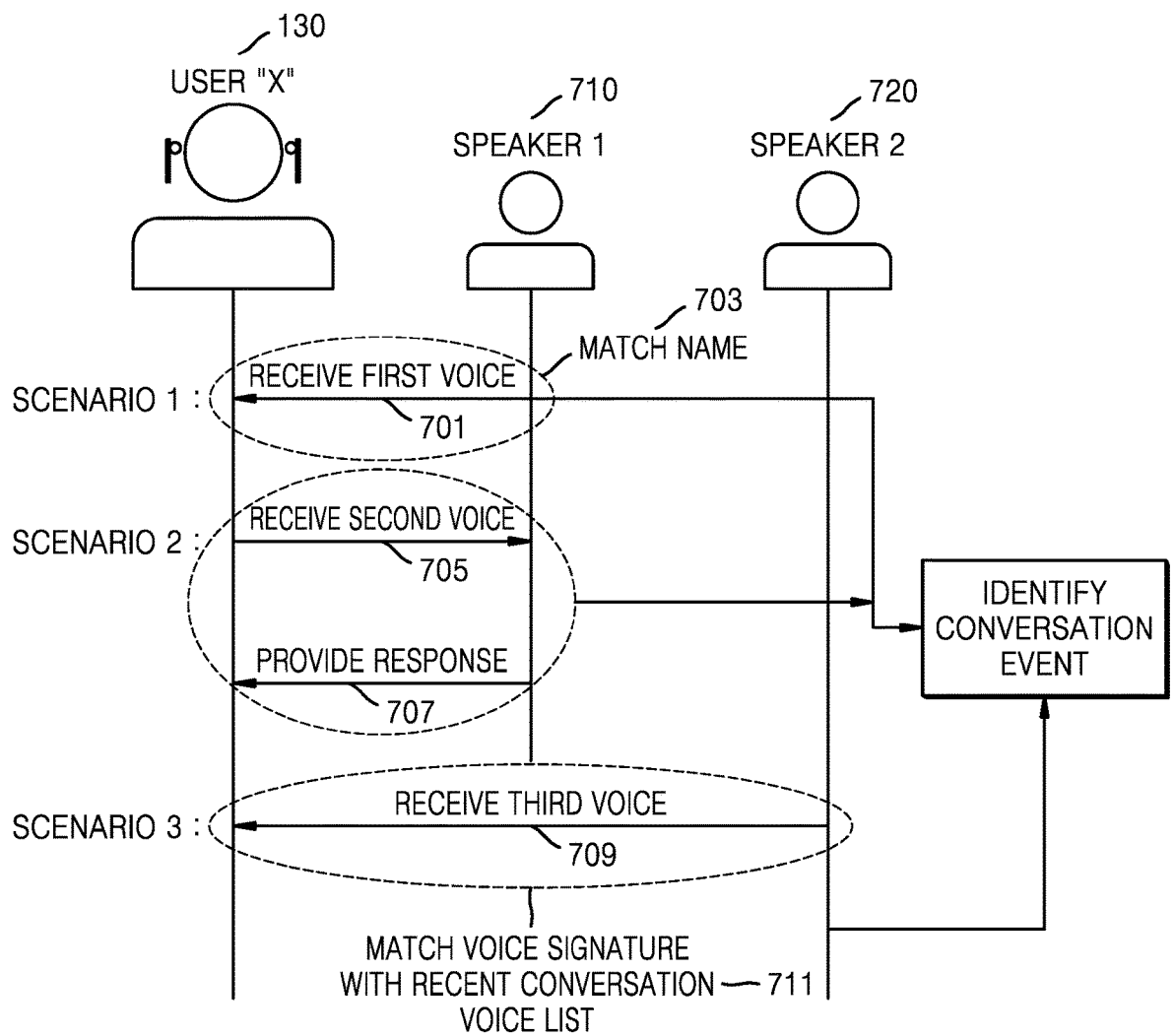
FIG. 7 is a schematic diagram illustrating identification of a conversation state by a wearable device, according to an embodiment of the disclosure.

FIG. 7 is a schematic diagram illustrating identification of a conversation state by a wearable device, according to an embodiment of the disclosure.

Referring to FIG. 7, a conversation event between the user 130 of the wearable device 110 (hereinafter, a user "X" (130)) and a speaker 1(710) or a conversation event between the user 130 of the wearable device 110 and a speaker 2(720) may be identified. For example, in scenario 1, the user X(130) may receive a first voice from the speaker 1(710) (operation 701). The wearable device 110 may match the name of the speaker 1(710) based on a voice signature of the speaker 1(710) included in the received first voice (operation 703). In other words, the wearable device 110 may compare the voice signature included in the first voice with a pre-stored voice signature, and, when the voice signature included in the first voice matches with the pre-stored voice signature, may identify the conversation event between the user X(130) and the speaker 1(710).

In scenario 2, the user X(130) may transmit a second voice to the speaker 1(710) (operation 705). In other words, the user X(130) may start a conversation with the speaker 1(710). The speaker 1(710) may receive the second voice from the user X(130), and may provide a response to the received second voice (operation 707). After receiving the response from the speaker 1(710), the wearable device 110 may identify the conversation event between the user X(130) and the speaker 1(710).

In scenario 3, the user X(130) may receive a third voice from the speaker 2(720) (operation 709). According to an embodiment, the third voice may include a voice signature of the speaker 2(720). The wearable device 110 may match the voice signature of the speaker 2(720) included in the received third voice with a recent conversation voice list (operation 711). For example, the wearable device 110 may determine whether the voice signature of the speaker 2(720) included in the received third voice is identical with a voice signature on the recent conversation voice list stored in the wearable device 110. When the voice signature of the speaker 2(720) is identical with, namely, matches with, at least one of the voice signatures on the recent conversation voice list, the wearable device 110 may identify a conversation event between the user X(130) and the speaker 2(720). According to an embodiment, the conversation event may be referred to as a conversation state or a conversation relation.

Figure 8:
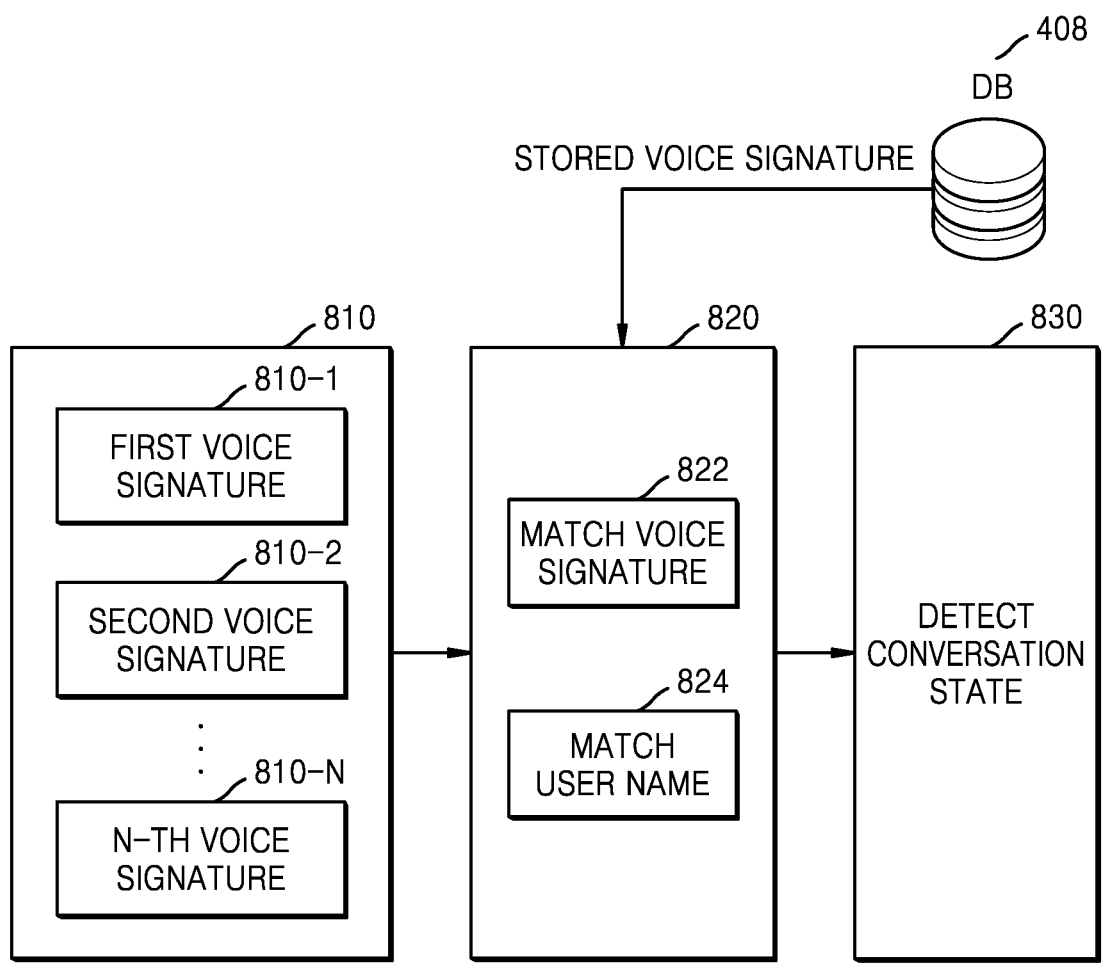
FIG. 8 is a schematic diagram of conversation state identification by a wearable device, according to an embodiment of the disclosure.

FIG. 8 is a schematic diagram of conversation state identification by a wearable device, according to an embodiment of the disclosure.

Referring to FIG. 8, the wearable device 110 may obtain a plurality of voice signatures 810. For example, the wearable device 110 may obtain a first voice signature 810-1, a second voice signature 810-2, and an N-th voice signature 810-N from the separated voice 630 of each speaker of FIG. 6. The wearable device 110 may perform voice signature matching by using a voice signature matching module 820. For example, the wearable device 110 may match the obtained plurality of voice signatures 810 with the voice signatures stored in the DB 408 (operation 822). In other words, the wearable device 110 may identify a voice signature identical with a voice signature stored in the DB 408, from among the plurality of voice signatures 810.

According to an embodiment, the wearable device 110 may match the identified voice signature with a speaker's name (operation 824). The speaker's name may be stored in the DB 408 along with the voice signature of the speaker. According to an embodiment, the DB 408 may be included in the wearable device 110, may be included in the user terminal 120 connected to the wearable device 110 in a wired or wireless manner, or may be included in another storage.

When at least one of the obtained voice signatures matches with a pre-stored voice signature, the wearable device 110 may detect a conversation state of the user 130 (operation 830). When the conversation state is detected, the wearable device 110 may determine the operation mode of the wearable device 110 to be the conversation mode, and may perform a preset operation. For example, the wearable device 110 may perform at least one operation of canceling noise of the input received by the wearable device 110, amplifying the voice of the speaker in a conversation relation with the user 130, or adjusting the volume of content reproduced by the wearable device 110 so that the user 130 may hear the voice of the speaker. For example, the wearable device 110 may receive the voice of the speaker through a microphone. The wearable device 110 may amplify the received voice of the speaker and output an amplified voice of the speaker. According to an embodiment, the voice of the speaker may be amplified to be louder than a volume of an audio of a content reproduced by the wearable device 110.

Figure 9:
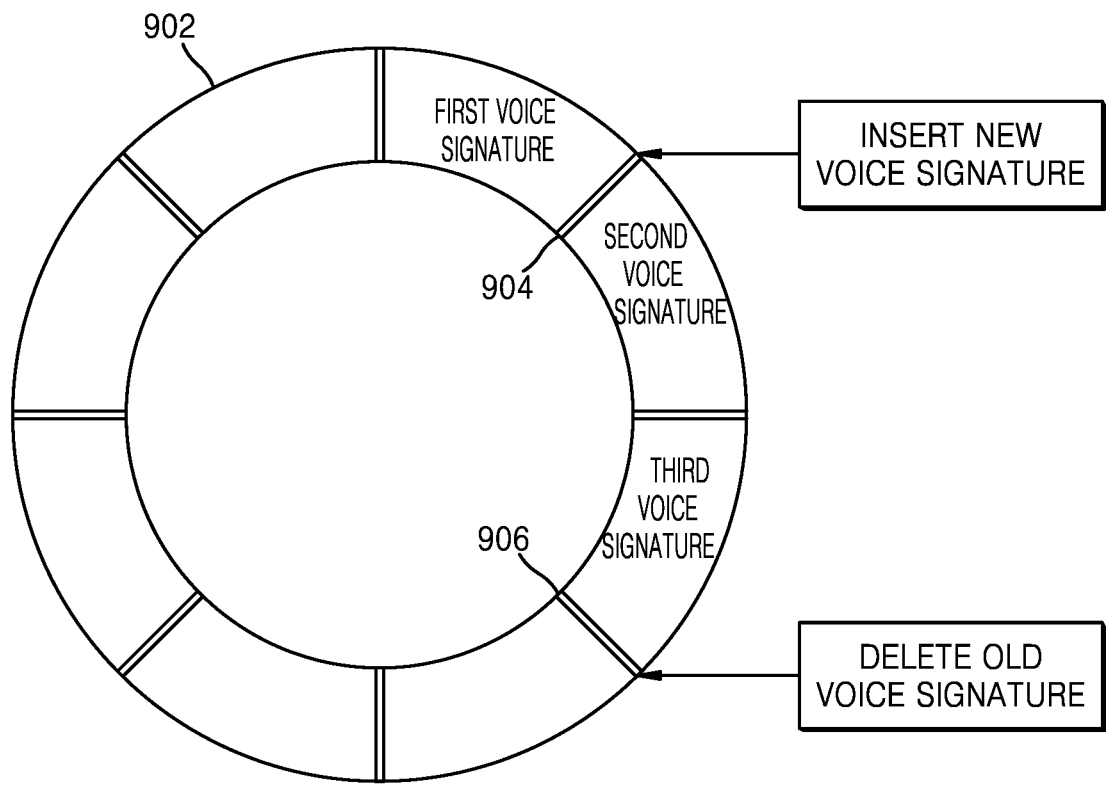
FIG. 9 illustrates a method in which a wearable stores voice signatures, device according to an embodiment of the disclosure.

FIG. 9 illustrates a method in which a wearable stores voice signatures, device according to an embodiment of the disclosure.

Referring to FIG. 9, a voice signature of the user 130 of the wearable device 110 or a speaker who talks with the user 130 may be stored in a circular data storage 902. Although FIG. 9 illustrates a circular data structure, a data structure in which voice signatures are stored is not limited to the circular data structure, and various modifications thereto may be made. According to an embodiment, a first voice signature, a second voice signature, and a third voice signature may be stored in the circular data storage 902.

The wearable device 110 may insert a new voice signature into a first point 904 between the first voice signature and the second voice signature. For example, the new voice signature may refer to a voice signature not stored in the existing circular data storage 902. According to an embodiment, the new voice signature may refer to a most recent voice signature, and the most recent voice signature may be stored in the circular data storage 902. According to an embodiment, the wearable device 110 may delete a voice signature that is old based on a second point 906 after the third voice signature. For example, the wearable device 110 may delete at least one stored voice signature after the second point 906.

As described above, a recent voice signature may be stored in the storage of the wearable device 110, and the old voice signature may be deleted. Accordingly, a storage space of the wearable device 110 that may be limited may be efficiently utilized.

Figure 10:
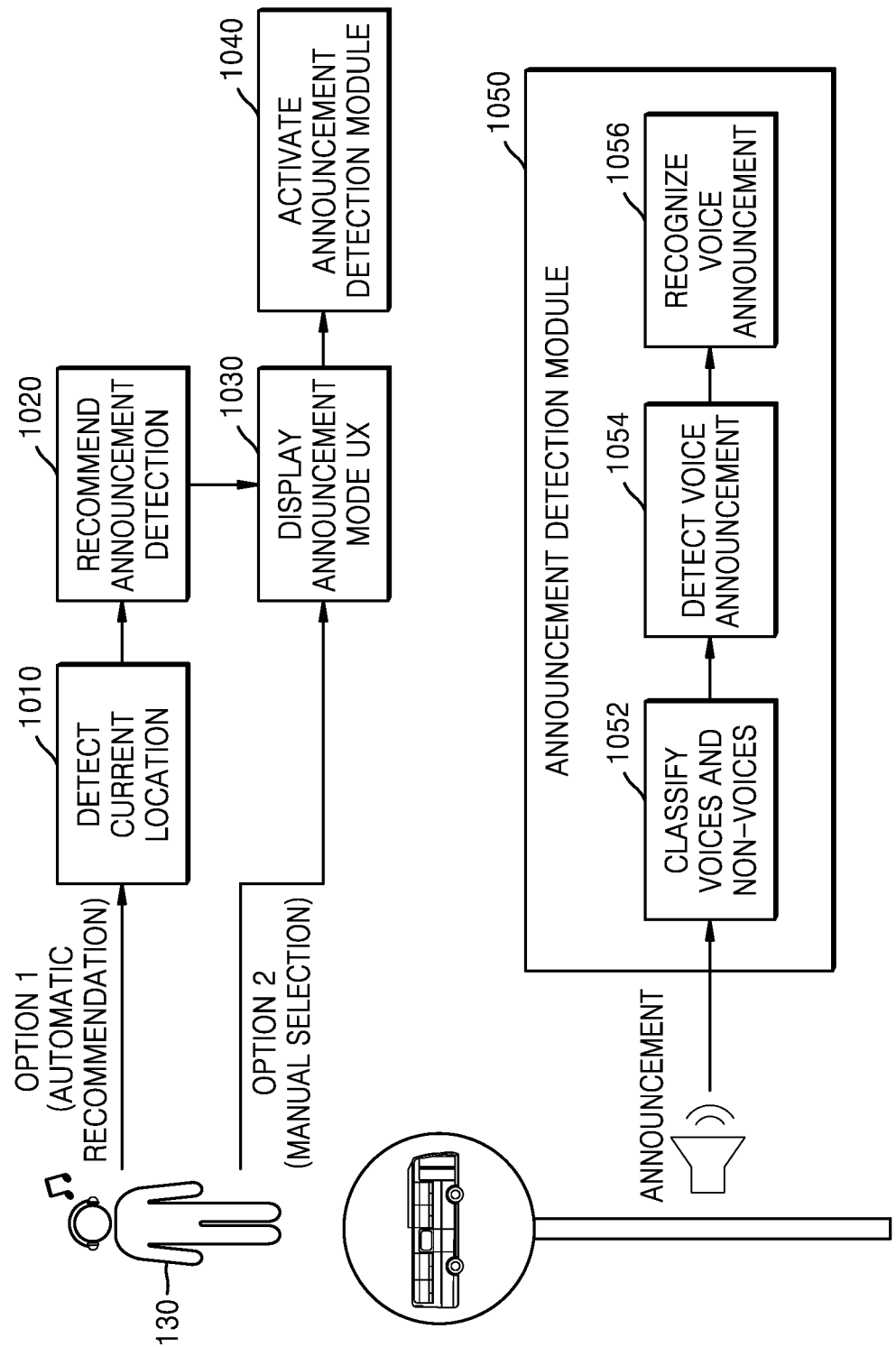
FIG. 10 is a schematic diagram of an overall procedure in which a wearable device operates when an operation mode of the wearable device is an announcement mode, according to an embodiment of the disclosure.

An overall process and a detailed process of an operation of the wearable device 110 in the conversation mode have been described above with reference to FIGS. 4 through 9. According to an embodiment, the wearable device 110 may detect a conversation between the user 130 and a speaker, and may perform an operation of receiving an announcement broadcast in a place such as a bus station, a subway station, or a train station and performing an operation corresponding to the announcement mode, in addition to performing an operation corresponding to the conversation mode. For example, when the user 130 wearing the wearable device 110 is in a subway station, an announcement that a subway train is approaching the subway station may be broadcast in the subway station. The wearable device 110 may detect the announcement broadcast in the subway station, and may perform at least one operation of canceling noise of a received input and adjusting a volume of an audio of a content reproduced by the wearable device 110. FIG. 10, which will be described later, illustrates a procedure of an operation of the wearable device 110 in the announcement mode.

FIG. 10 is a schematic diagram of an overall procedure in which a wearable device operates when an operation mode of the wearable device is an announcement mode, according to an embodiment of the disclosure.

Referring to FIG. 10, the user 130 of the wearable device 110 may automatically or manually select the announcement mode. According to an embodiment, the wearable device 110 may automatically recommend the announcement mode to the user 130, as option 1. For example, when the wearable device 110 is at a specific location such as a bus station or a subway station, the wearable device 110 may automatically recommend an operation in the announcement mode without inputs of the user 130. According to an embodiment, the wearable device 110 may allow the user 130 to manually select the announcement mode, as option 2. For example, the wearable device 110 may provide a user interface capable of selecting the announcement mode, on a display of the wearable device 110 or a display of the user terminal 120 connected to the wearable device 110 by wire or wirelessly. The above-described operation procedure of the wearable device 110 in option 1 or option 2 will be described in detail below.

In option 1, the wearable device 110 may detect a current location (operation 1010). According to an embodiment, the wearable device 110 may detect a current location of the wearable device 110 by using a location measurement technique. For example, the location measurement technique may include a location measurement technique using Global Positioning System (GPS), Assisted GPS (A-GPS), Wibro™, or Wi-Fi™. According to an embodiment, the wearable device 110 or the user terminal 120 may include a corresponding GPS hardware and/or software component such as a GPS sensor configured to implement the location measurement technique. According to an embodiment, the wearable device 110 may detect that the wearable device 110 is currently located in a bus station, a subway station, a train station, or an airport. After the current location of the wearable device 110 is detected, the wearable device 110 may recommend announcement detection (operation 1020). In other words, the wearable device 110 may recommend a user to detect an announcement broadcast at the current location of the wearable device 110, based on the current location. For example, the announcement broadcast at the current location may refer to an announcement of a facility such as a bus station, a subway station, a train station, or an airport.

The wearable device 110 may display an announcement mode UX (operation 1030). For example, the wearable device 110 may determine to recommend the user 130 to detect an announcement, and may display a user interface for selecting the announcement mode on the display of the wearable device 110 or the display of the user terminal 120. To activate the announcement mode, the user 130 may select the announcement mode UX displayed on the display of the wearable device 110 or the display of the user terminal 120.

The wearable device 110 may activate an announcement detection module, based on an input of the user 130 (operation 1040). For example, when the announcement mode UX is selected by the user 130 by touching, clicking, or pressing a button, the wearable device 110 may activate an announcement detection module 1050 representing detection of an announcement. According to an embodiment, the announcement detection module 1050 may be included in the wearable device 110 or the user terminal 120.

An operation method of the announcement detection module 1050 according to activation of the announcement detection module 1050 will now be described. According to an embodiment, when an announcement is broadcast in a bus station, the announcement detection module 1050 may classify voices and non-voices from the broadcast announcement (operation 1052). According to an embodiment, at least one of the classified voices may include an announcement signature. The announcement detection module 1050 may detect a voice announcement for the classified voices (operation 1054). For example, the voice announcement may refer to a voice including an announcement signature from among the classified voices obtained by the voice and non-voice classification. Thereafter, the announcement detection module 1050 may recognize the voice announcement (operation 1056). In other words, the announcement detection module 1050 may recognize the voice announcement by detecting the voice announcement including the announcement signature. When the voice announcement is recognized, the wearable device 110 may perform at least one operation of canceling noise from the received input, and an operation of adjusting a volume of an audio of a content reproduced by the wearable device 110.

Figure 11:
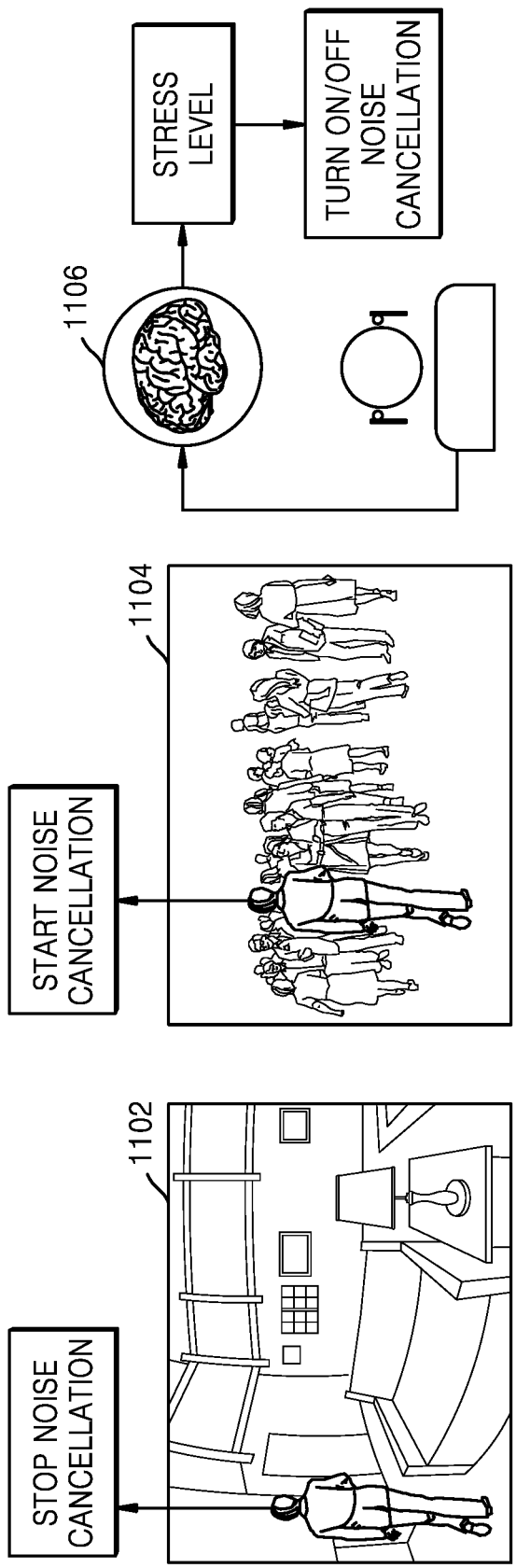
FIG. 11 is a schematic diagram of a scenario where a wearable device operates in a power control mode, according to an embodiment of the disclosure.

FIG. 11 is a schematic diagram of a scenario where a wearable device operates in a power control mode, according to an embodiment of the disclosure.

Referring to FIG. 11, because a noise cancellation function requires much power consumption, the wearable device 110 may analyze a surrounding environment of the wearable device 110 in order to reduce power consumption. The wearable device 110 may turn on or off the noise cancellation function, based on the state of the analyzed surrounding environment. For example, in a first environment 1102, the wearable device 110 may identify that the surrounding environment of the wearable device 110 is quiet. According to an embodiment, the wearable device 110 may receive a surrounding sound as an input. When the magnitude of the received input is less than a threshold, the wearable device 110 may determine that the surrounding environment of the wearable device 110 is quiet. When it is determined that the surrounding environment is quiet, the wearable device 110 may stop noise cancellation.

In a second environment 1104, the wearable device 110 may identify that the surrounding environment of the wearable device 110 is not quiet. According to an embodiment, the wearable device 110 may receive a surrounding sound as an input. When the magnitude of the received input is equal to or greater than the threshold, the wearable device 110 may determine that the surrounding environment of the wearable device 110 is not quiet. When it is determined that the surrounding environment is not quiet, the wearable device 110 may start noise cancellation.

According to an embodiment, the wearable device 110 may monitor a users stress level by using brainwaves of the user 130. Based on the monitored user's stress level and pre-determined users preference, noise cancellation may be activated or deactivated. For example, the wearable device 110 may detect brainwaves emitted by the brain 1106 of the user 130, and may determine a stress level of the user 130 by using characteristics of the detected brainwaves.

According to an embodiment, the brainwaves may be detected through an electroencephalography (EEG) sensor. The EEG sensor may be included in the wearable device 110 or the user terminal 120. When the stress level of the user is equal to or greater than a threshold, the wearable device 110 may turn on noise cancellation. When the stress level of the user is less than the threshold, the wearable device 110 may turn off noise cancellation. According to an embodiment, the wearable device 110 may adjust an audio sub-sampling rate, based on the state of the analyzed surrounding environment of the wearable device 110, in order to achieve power saving. According to an embodiment, the wearable device 110 may detect the brainwaves emitted by the brain 1106 of the user 130, and may determine a sleep stage of the user 130, based on the detected brainwaves. The wearable device 110 may activate or deactivate noise cancellation, based on the determined sleep stage of the user 130.

Figure 12:
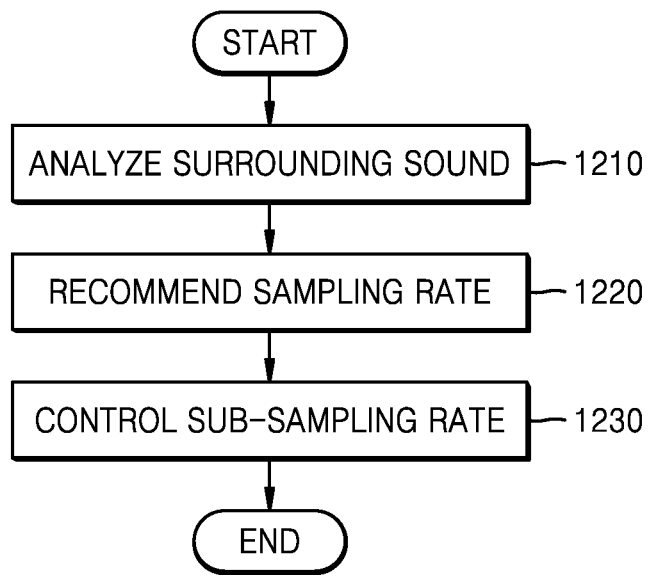
FIG. 12 is a flowchart of an operation method of a wearable device when the operation mode of the wearable device is a power control mode, according to an embodiment of the disclosure.

FIG. 12 is a flowchart of an operation method of a wearable device when the operation mode of the wearable device is a power control mode, according to an embodiment of the disclosure.

Referring to FIG. 12, in operation 1210, the wearable device 110 may analyze a surrounding sound. The wearable device 110 may receive the surrounding sound as an input. According to an embodiment, when a magnitude of the received input is less than a threshold, the wearable device 110 may determine that the surrounding environment of the wearable device 110 is quiet. According to an embodiment, when the magnitude of the received input is equal to or greater than the threshold, the wearable device 110 may determine that the surrounding environment of the wearable device 110 is not quiet. According to an embodiment, when a voice signature of a speaker included in the received input matches with a pre-stored voice signature, the wearable device 110 may determine a conversation state between the user 130 and the speaker.

In operation 1220, the wearable device 110 may recommend a sampling rate. For example, the wearable device 110 may determine a state of the surrounding environment of the wearable device 110 by using a surrounding sound analysis, and may determine an audio sub-sampling or sampling rate according to the determined state. According to an embodiment, when the surrounding environment of the wearable device 110 is quiet or a conversation between the user 130 and the speaker does not continue, the wearable device 110 may recommend an audio sub-sampling rate that is less than a threshold. According to an embodiment, when the surrounding environment of the wearable device 110 is not quiet or a conversation between the user 130 and the speaker continues, the wearable device 110 may recommend an audio sub-sampling rate that is equal to or greater than the threshold.

In operation 1230, the wearable device 110 may control a sub-sampling rate. For example, when the surrounding environment of the wearable device 110 is quiet or a conversation between the user 130 and the speaker does not continue, the wearable device 110 may reduce the audio sub-sampling rate. When the surrounding environment of the wearable device 110 is not quiet or a conversation between the user 130 and the speaker continues, the wearable device 110 may increase the audio sub-sampling rate. As described above, the wearable device 110 may adaptively adjust the audio sub-sampling rate by analyzing the surrounding sound. Due to the adaptive audio sub-sampling speed adjustment, power consumption of the wearable device 110 may be saved.

Figure 13:
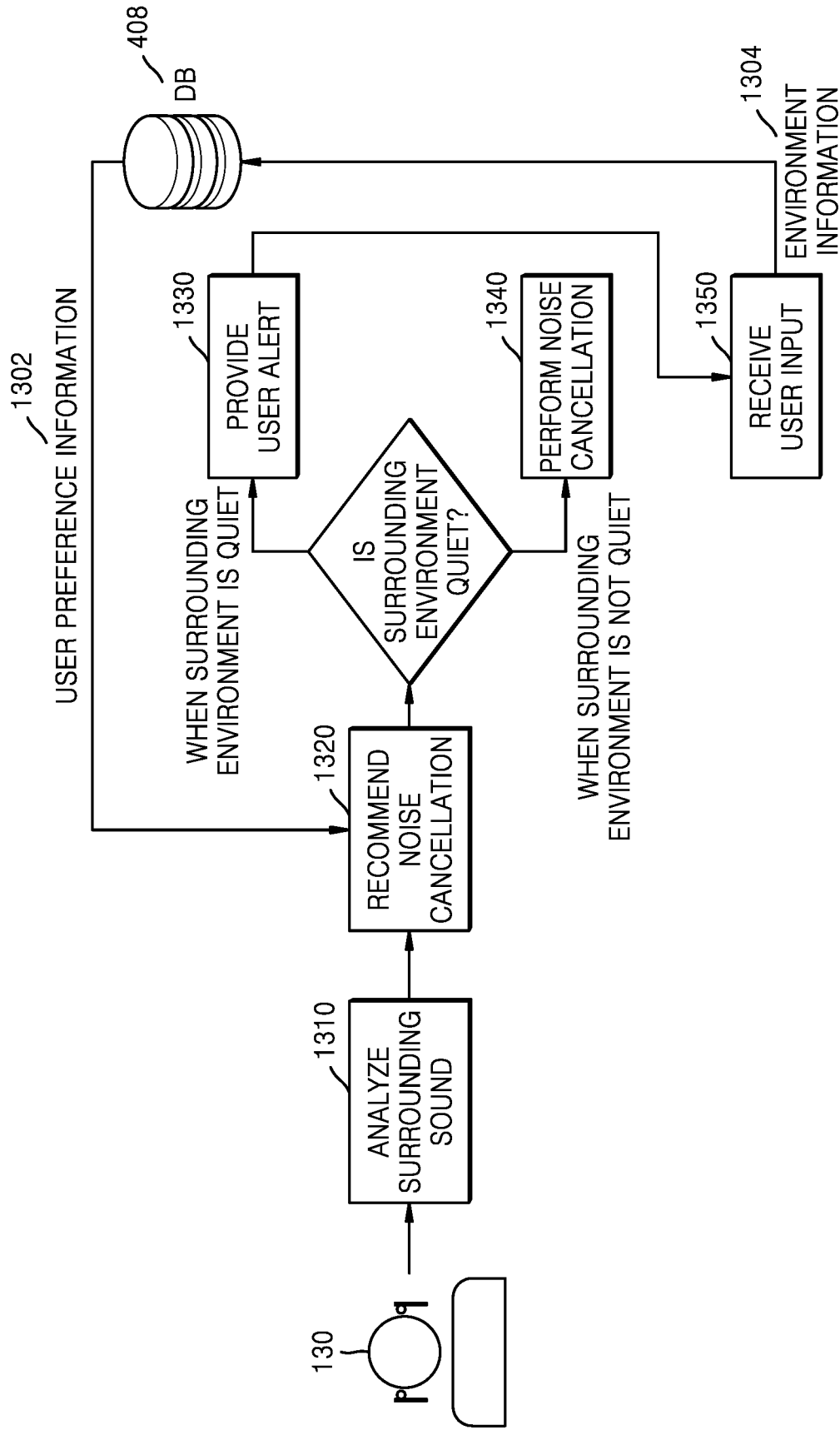
FIG. 13 is a flowchart of an overall procedure in which a wearable device operates when an operation mode of the wearable device is a power control mode, according to an embodiment of the disclosure.

FIG. 13 is a flowchart of an overall procedure in which a wearable device operates when an operation mode of the wearable device is a power control mode, according to an embodiment of the disclosure.

Referring to FIG. 13, the wearable device 110 may analyze a surrounding sound of the wearable device 110 (operation 1310). In other words, the wearable device 110 may identify a surrounding environment of the wearable device 110 by analyzing the surrounding sound. For example, the wearable device 110 may receive the surrounding sound as an input. When a magnitude of the received input is less than a threshold, the wearable device 110 may determine that the surrounding environment of the wearable device 110 is quiet. When the magnitude of the received input is equal to or greater than the threshold, the wearable device 110 may determine that the surrounding environment of the wearable device 110 is not quiet.

The wearable device 110 may recommend noise cancellation, based on the identified surrounding environment of the wearable device 110. For example, the wearable device 110 may recommend noise cancellation according to whether the identified surrounding environment of the wearable device 110 is quiet or not (operation 1320). User preference information 1302 stored in the DB 408 may be used to recommend noise cancellation. For example, the user preference information 1302 may include information representing that a user prefers a quiet environment or a noisy environment. According to an embodiment, when the surrounding environment of the wearable device 110 is quiet, the wearable device 110 may provide a user alert (operation 1330). For example, the wearable device 110 may provide an alert indicating a turn off operation of noise cancellation to the wearable device 110 or the user terminal 120 so that the user 130 determines whether to perform noise cancellation. According to an embodiment, when the surrounding environment of the wearable device 110 is analyzed as a quiet environment, the wearable device 110 may provide a user alert for turning off an on-going noise cancellation operation. For example, the user alert may include a pop-up window displaying a phrase such as "Will you turn off noise cancellation?", and a first button (e.g., yes) and a second button (e.g., no) enabling the user 130 to select whether to turn off noise cancellation. The first button and the second button may be included in the pop-up window, but embodiments of the disclosure are not limited thereto. According to an embodiment, operation 1320 of recommending noise cancellation may be included in operation 1310 of analyzing the surrounding sound. An operation of determining whether the surroundings of the wearable device 110 are quiet may be included in operation 1310 of analyzing the surrounding sound, or may be performed before operation 1320 of recommending noise cancellation.

According to an embodiment, when the user preference information 1302 indicates that the user 130 prefers a noisy environment, even when the surrounding environment of the wearable device 110 is not quiet, the wearable device 110 may provide an alert for turning off noise cancellation to the wearable device 110 or the user terminal 120. According to an embodiment, the wearable device 110 may receive a user input (operation 1350). For example, the wearable device 110 may receive a user input to the display of the wearable device 110. The user 130 may turn off noise cancellation of the wearable device 110 according to the alert, or may ignore the alert.

The wearable device 110 may store, in the DB 408, environment information 1304 indicating a current surrounding environment of the wearable device 110. According to an embodiment, the environment information 1304 stored in the DB 408 may be used to generate the user preference information 1302 during recommendation of noise cancellation. According to an embodiment, when the surrounding environment of the wearable device 110 is not quiet, the wearable device 110 may perform noise cancellation (operation 1340). According to an embodiment, when the user preference information 1302 indicates that the user 130 prefers a quiet environment, even when the surrounding environment of the wearable device 110 is quiet, the wearable device 110 may perform noise cancellation.

According to an embodiment, when it is determined whether noise cancellation by the wearable device 110 is performed, a priority between the identified surrounding environment of the wearable device 110 and the user preference information 1302 may be previously determined. For example, when a priority of the user preference information 1302 is higher than a priority of the identified surrounding environment of the wearable device 110, the wearable device 110 may determine whether to perform noise cancellation, based on the user preference information 1302, regardless of the identified surrounding environment of the wearable device 110. According to an embodiment, when the priority of the identified surrounding environment of the wearable device 110 is higher than the priority of the user preference information 1302, the wearable device 110 may determine whether to perform noise cancellation, based on the identified surrounding environment of the wearable device 110, regardless of the user preference information 1302.

According to an embodiment, the wearable device 110 may monitor a health state of the user 130 wearing the wearable device 110. For example, the wearable device 110 may monitor an ear health state of the user 130 by using acoustic reflectometry. The wearable device 110 may also monitor sleep-related physiological signals from brainwaves of the user 130. The wearable device 110 may identify a sleep pattern of the user 130 by monitoring the physiological signals. The wearable device 110 may detect the stress level of the user 130 by analyzing the brainwaves of the user 130. Embodiments of monitoring the health state of the user 130 by using the wearable device 110 will now be described with reference to FIGS. 14 and 15.

Figure 14:
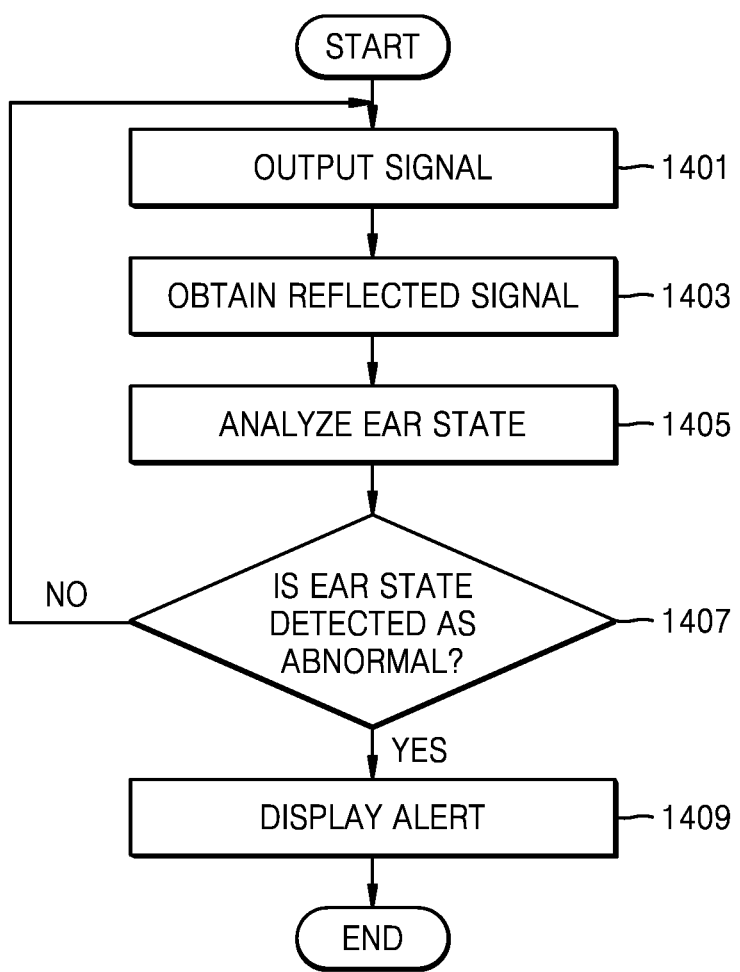
FIG. 14 is a flowchart of an operation method of a wearable device when the operation mode of the wearable device analyzes an ear health state, according to an embodiment of the disclosure.

FIG. 14 is a flowchart of an operation method of a wearable device when the operation mode of the wearable device analyzes an ear health state, according to an embodiment of the disclosure.

Referring to FIG. 14, in operation 1401, the wearable device 110 may output a signal. For example, the wearable device 110 may output a sound signal to ears of the user 130 of the wearable device 110 by using acoustic reflectometry. The output sound signal may be reflected by the ears of the user 130.

In operation 1403, the wearable device 110 may obtain a reflected signal. For example, the wearable device 110 may obtain a reflected sound signal generated by reflecting the output sound signal within the ears of the user 130. According to an embodiment, the reflected sound signal may vary according to the ear structure of the user 130 and an ear health state thereof. A method of outputting the sound signal and obtaining the reflected sound signal as described above may be defined as acoustic reflectometry.

In operation 1405, the wearable device 110 may analyze the ear state. For example, the wearable device 110 may analyze the ear state of the user 130 by using the reflected sound signal obtained via acoustic reflectometry. According to an embodiment, an AI model may be used to analyze the ear state of the user 130. For example, the wearable device 110 may determine the ear state of the user 130 corresponding to the reflected sound signal, based on data trained through machine learning or deep learning.

In operation 1407, the wearable device 110 may detect whether the ear state is abnormal. For example, during the ear state analysis using the AI model, when the reflected sound signal corresponds to an abnormal ear state, the wearable device 110 may detect that the ears of the user 130 are abnormal. When the reflected sound signal corresponds to a non-abnormal ear state, the wearable device 110 may detect that the ears of the user 130 are not abnormal. According to an embodiment, the abnormal hear state may include middle ear infection or middle ear effusion. When an abnormality in the ear state is not detected, the wearable device 110 may perform operation 1401 again. When an abnormality in the ear state is detected, the wearable device 110 may perform operation 1409.

In operation 1409, the wearable device 110 may display an alert. For example, when an abnormality in the ear state is detected, the wearable device 110 may display a result of the detection on the wearable device 110 or the user terminal 120. According to an embodiment, the wearable device 110 may display a user interface representing that the ear state of the user 130 is abnormal, on the wearable device 110 or the user terminal 120. The user 130 may ascertain that the ear state of the user 130 is abnormal, by checking the alert displayed on the wearable device 110 or the user terminal 120.

Figure 15:
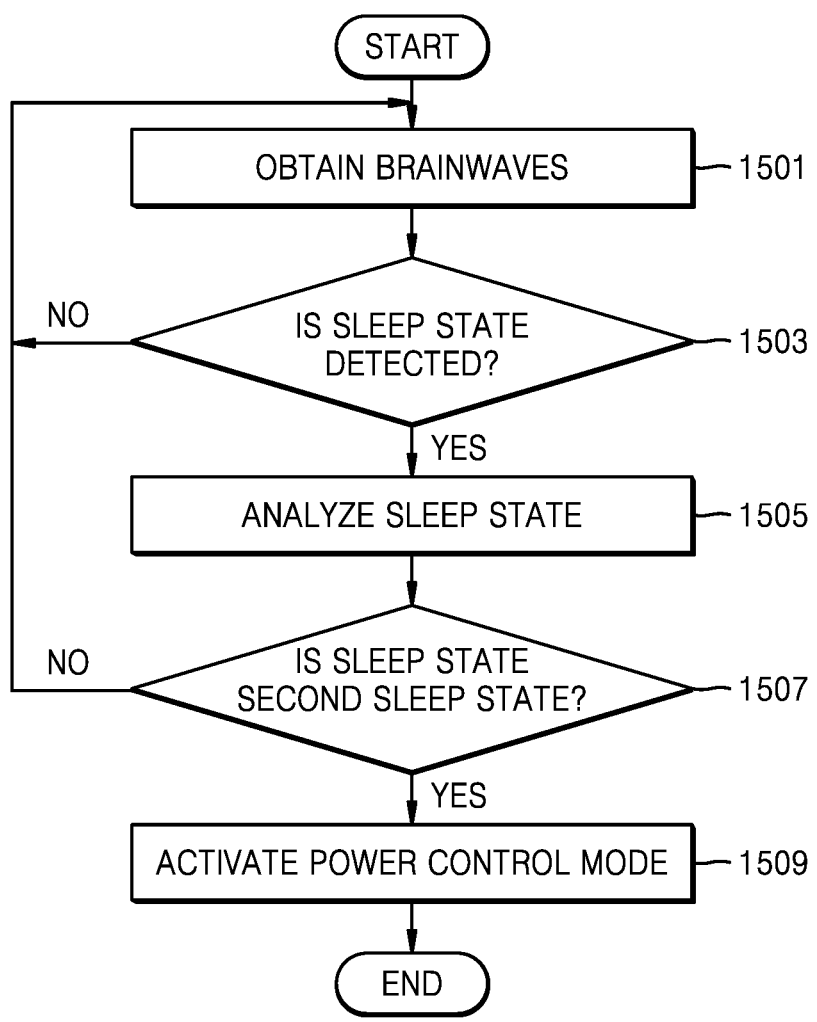
FIG. 15 is a flowchart of an operation method of a wearable device that activates a power control mode by analyzing a sleep state of the wearable device, according to an embodiment of the disclosure.

FIG. 15 is a flowchart of an operation method of a wearable device that activates a power control mode by analyzing a sleep state of the wearable device, according to an embodiment of the disclosure.

Referring to FIG. 15, in operation 1501, the wearable device 110 may obtain brainwaves. For example, the wearable device 110 may obtain brainwaves from a brain of the user 130 by using the EEG sensor. The EEG sensor may be included in the wearable device 110.

In operation 1503, the wearable device 110 may determine whether the sleep state is detected. For example, the wearable device 110 may determine whether the state of the user 130 is in sleep or awake. When the sleep state of the user 130 is not detected, namely, when the user 130 is awake, the wearable device 110 may perform operation 1501 again. When the sleep state of the user 130 is detected, namely, when the user 130 is in sleep, the wearable device 110 may perform operation 1505.

In operation 1505, the wearable device 110 may analyze the sleep state. For example, the wearable device 110 may analyze and record a sleep quality of the user 130 or classify the sleep states of the user 130 according to types. For example, the types of the sleep states of the user 130 may include a first sleep state or a second sleep state. According to an embodiment, the first sleep state may refer to an REM sleep representing a shallow sleep close to being awake. According to an embodiment, the second sleep state may refer to a deep sleep state. For example, the deep sleep state may refer to a non-REM sleep corresponding to a deeper sleep state than the REM sleep. The wearable device 110 may analyze the sleep state of the user 130, based on the obtained brainwaves.

In operation 1507, the wearable device 110 may determine whether the sleep state is the second sleep state. For example, the wearable device 110 may determine whether the sleep state of the user is an REM sleep. When the sleep state of the user 130 is not the second sleep state, the wearable device 110 may perform operation 1501 again. When the sleep state of the user 130 is the second sleep state, the wearable device 110 may perform operation 1509.

In operation 1509, the wearable device 110 may activate the power control mode. According to an embodiment, when the sleep state of the user 130 is the second sleep state, the user 130 is in a deep sleep, and thus noise cancellation may not be needed. Thus, the wearable device 110 may activate the power control mode. The wearable device 110 may save power used for real-time power control, by turning off noise cancellation, in the power control mode. Although not shown in FIG. 15, the wearable device 110 may activate the power control mode, turn off noise cancellation, and then perform operation 1501 again to obtain brainwaves. The wearable device 110 may analyze the stress level of the user 130 by using the brainwaves of the user 130 obtained using an EEG sensor. As shown in FIG. 15, the wearable device 110 may sense the brainwaves of the user 130 of the wearable device 110, may identify the sleep state of the user 130 by analyzing the sensed brainwaves, and may perform noise cancellation based on the identified sleep state.

Figure 16:
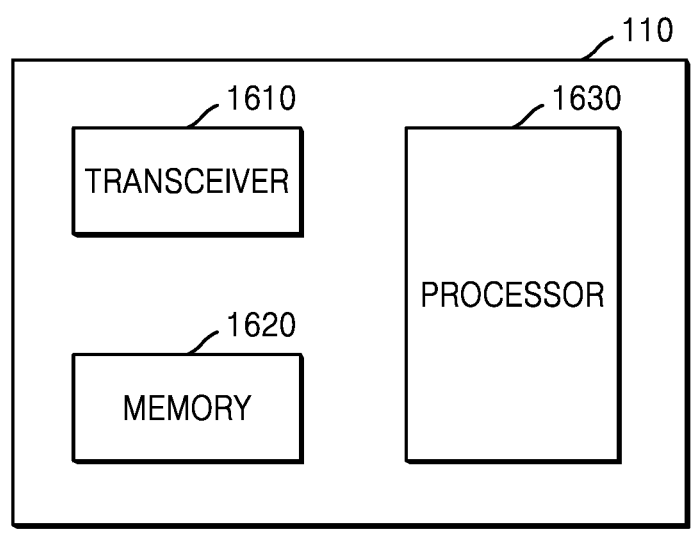
FIG. 16 is a block diagram of a wearable device, according to an embodiment of the disclosure.

FIG. 16 is a block diagram of a wearable device, according to an embodiment of the disclosure.

Referring to FIG. 16, the wearable device 110 may include a transceiver 1610, a memory 1620, and a processor 1630. All of the components illustrated in FIG. 16 are not essential components of the wearable device 110. More or less components than those illustrated in FIG. 16 may constitute the wearable device 110.

According to an embodiment, the transceiver 1610 may communicate with the user terminal 120 connected to the wearable device 110 in a wired or wireless manner or with another electronic device. For example, the transceiver 1610 may receive a surrounding sound of the wearable device 110 as an input, and may receive user input information input to the user terminal 120. According to an embodiment, the transceiver 1610 may output a sound signal in order to use acoustic reflectometry. The transceiver 1610 may receive a reflected sound signal generated by reflecting the output sound signal within the ears of the user 130. The transceiver 1610 may include a microphone or corresponding component to receive the surrounding sound and the reflected sound signal, and may also include any one or any combination of a digital modem, a radio frequency (RF) modem, a Wi-Fi™ chip, and related software and/or firmware to communicate with the user terminal 120.

The memory 1620 may install and store various types of data such as a program (such as, an application) and a file. The processor 1630 may access and use the data stored in the memory 1620, or may store new data in the memory 1620. According to an embodiment, the memory 1620 may include the DB 408. According to an embodiment, the memory 1620 may store a voice signature of the user 130 or the speaker extracted from the surrounding sound of the wearable device 110. According to an embodiment, the memory 1620 may store user preference information for recommending noise cancellation.

The processor 1630 may control an overall operation of the wearable device 110 and may include at least one of processors or microprocessors such as a central processing unit (CPU) and a graphic processing unit (GPU). The processor 1630 may control other components included in the wearable device 110 to perform an operation for driving the wearable device 110. For example, the processor 1630 may execute the program stored in the memory 1620, read the file stored in the memory 1620, or store a new file. According to an embodiment, the processor 1630 may perform an operation for driving the wearable device 110 by executing the program stored in the memory 1620.

Although not shown in FIG. 16, the wearable device 110 may further include a sensor unit. According to an embodiment, the sensor unit may include an EEG sensor. The sensor unit may sense brainwaves output from the brain of the user 130. According to an embodiment, the sensor unit may include a position sensor (for example, a GPS) for ascertaining a current location of the wearable device 110.

According to an embodiment, the wearable device 110 may include the transceiver 1610, the memory 1620 storing one or more instructions, and at least one processor 1630 that executes the one or more instructions to receive a surrounding sound of the wearable device 110 as an input, determine one from among a plurality of operation modes, based on the received input, and perform a preset operation according to the determined operation mode.

According to an embodiment, the plurality of operation modes may include at least one of a conversation mode representing a conversation state between a user of the wearable device 110 and a speaker, an announcement mode representing detection of an announcement from an external sound source, and a power control mode for controlling power consumption of the wearable device 110.

According to an embodiment, the processor 1630 of the wearable device 110 may execute the one or more instructions to determine the conversation mode from among the plurality of operation modes to be the operation mode when a voice signature detected from the received input matches with a pre-stored voice signature.

According to an embodiment, the processor 1630 of the wearable device 110 may execute the one or more instructions to update the pre-stored voice signature based on a voice signature detected from the received input when the detected voice signature matches with a pre-stored voice signature.

According to an embodiment, the processor 1630 of the wearable device 110 may execute the one or more instructions to determine the announcement mode from among the plurality of operation modes to be the operation mode when an announcement signature is detected from the received input.

According to an embodiment, the processor 1630 of the wearable device 110 may execute the one or more instructions to determine the power control mode from among the plurality of operation modes as the operation mode when the magnitude of the received input is less than a threshold.

According to an embodiment, the processor 1630 of the wearable device 110 may execute the one or more instructions to cancel noise from the received input, adjust the volume of content reproduced by the wearable device 110, and amplify a voice of a speaker when the wearable device 110 operates in the conversation mode.

According to an embodiment, the processor 1630 of the wearable device 110 may execute the one or more instructions to cancel noise from the received input and adjust the volume of content reproduced by the wearable device 110 when the wearable device 110 operates in the announcement mode.

According to an embodiment, the processor 1630 of the wearable device 110 may execute the one or more instructions to adjust a sampling rate of the received input, and deactivate noise cancellation when the wearable device 110 operates in the power control mode.

According to an embodiment, the wearable device 110 may further include a sensor unit, and the processor 1630 of the wearable device 110 may execute the one or more instructions to sense brainwaves of the user of the wearable device 110 by using the sensor unit, identify a sleep state of the user 130 by analyzing the sensed brainwaves, and perform noise cancellation, based on the identified sleep state.

Figure 17:
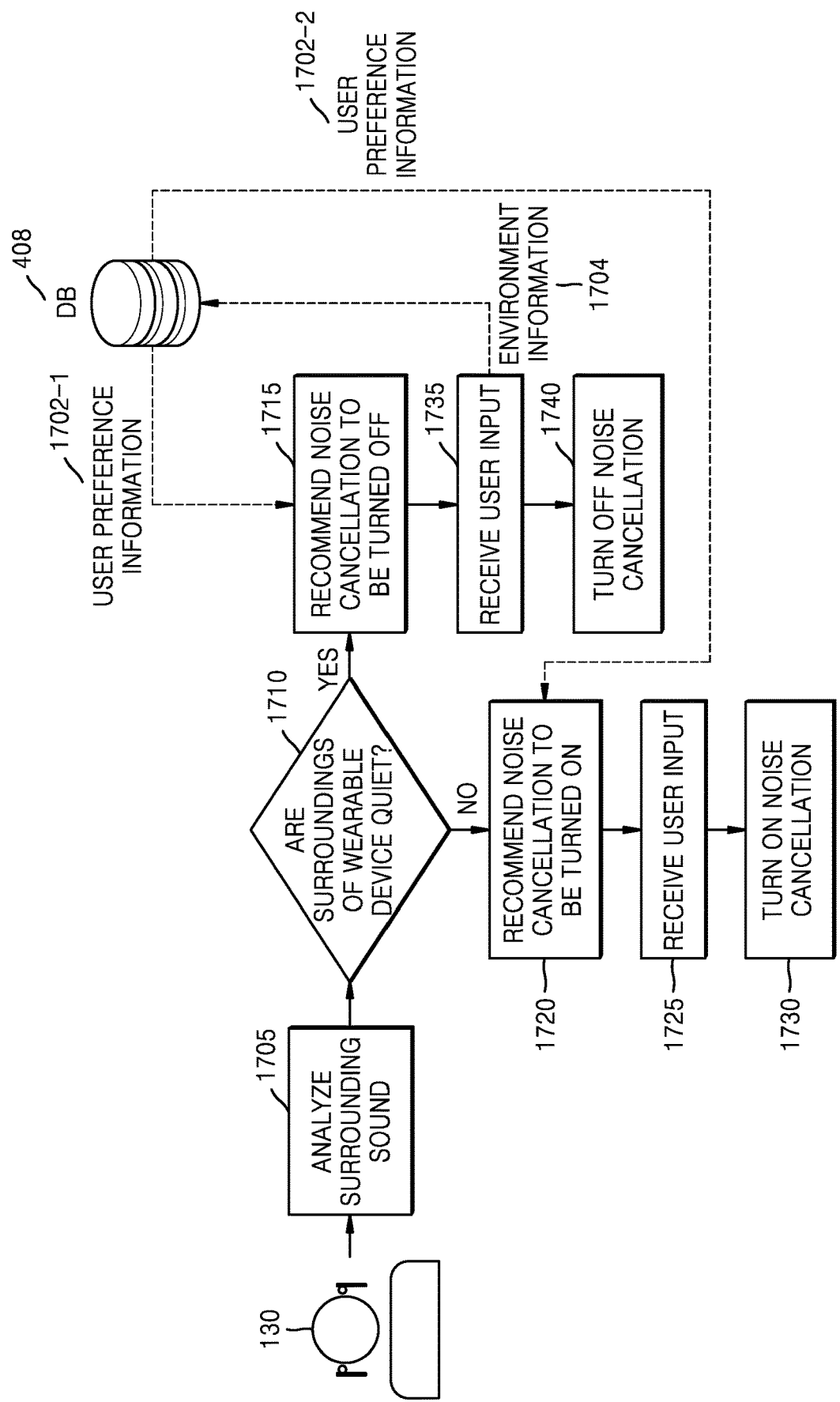
FIG. 17 is a flowchart of an operation of a wearable device when an operation mode of the wearable device is a power control mode, according to an embodiment of the disclosure.

FIG. 17 is a flowchart of an operation of a wearable device when an operation mode of the wearable device is a power control mode, according to an embodiment of the disclosure.

Referring to FIG. 17, the wearable device 110 may analyze a surrounding sound of the wearable device 110 (operation 1705). In other words, the wearable device 110 may identify a surrounding environment of the wearable device 110 by analyzing the surrounding sound. For example, the wearable device 110 may receive the surrounding sound as an input, and analyze whether the surrounding environment of the wearable device 110 is quiet or noisy.

The wearable device 110 may determine whether surroundings of the wearable device is quiet (operation 1710). For example, when a magnitude of a received input is less than a threshold, the wearable device 110 may determine that the surrounding environment of the wearable device 110 is quiet. When the magnitude of the received input is equal to or greater than the threshold, the wearable device 110 may determine that the surrounding environment of the wearable device 110 is not quiet. In other words, the wearable device 110 may determine that the surrounding environment is not quiet. Although operation 1710 is performed after operation 1705 in FIG. 17, embodiments of the disclosure are not limited thereto. In other words, operation 1705 and operation 1710 may be performed as a single operation. For example, the wearable device 110 may determine whether the surrounding environment of the wearable device 110 is quiet, by analyzing the surrounding sound of the wearable device 110. Operation 1710 may be included in operation 1705. For example, operation 1705 in which the wearable device 110 analyzes the surrounding sound includes operation 1710 of determining whether the surrounding environment of the wearable device 110 is quiet.

According to an embodiment, when the surrounding environment of the wearable device 110 is not quiet, the wearable device 110 may recommend noise cancellation to be turned on (operation 1720). For example, because the surrounding environment of the wearable device 110 is not quiet, the wearable device 110 may provide a message suggesting noise cancellation to be turned on, to the wearable device 110 or the user terminal 120. According to an embodiment, the message suggesting noise cancellation to be turned on may be displayed in a pop-up window form on the wearable device 110 or the user terminal 120. The pop-up window may include a noise cancellation turn-on recommendation phrase such as "Will you turn on noise cancellation?". The pop-up window may include a first button (e.g., yes) and a second button (e.g., no) enabling the user 130 to select whether to turn on noise cancellation. According to an embodiment, the message may be output in an audio message form by the wearable device 110, and thus, may be provided to the user 130. However, embodiments of the disclosure are not limited thereto. According to an embodiment, user preference information 1702-2 provided by the DB 408 may be used when the wearable device 110 recommends noise cancellation to be turned on. For example, even when the surrounding environment of the wearable device 110 is not quiet, when the user preference information 1702-2 represents that the user 130 prefers a noisy environment or does not prefer a quiet environment, the wearable device 110 may not recommend noise cancellation to be turned on.

The wearable device 110 may receive a user input (operation 1725). For example, the wearable device 110 receive an input of the user 130 regarding turn-on recommendation of noise cancellation, through the wearable device 110 or the user terminal 120. For example, when the user 130 wants to turn on noise cancellation, the user 130 may provide a user input by touching or clicking the first button representing that noise cancellation is turned on. When the user 130 does not want to turn on noise cancellation, the user 130 may provide a user input by touching or clicking the second button representing that noise cancellation is not turned on.

The wearable device 110 may turn on noise cancellation (operation 1730). For example, when the user 130 selects noise cancellation to be turned on, through a user input, the wearable device 110 may turn on a noise cancellation function of the wearable device 110. According to an embodiment, operation 1720 of recommending noise cancellation to be turned on and operation 1725 of receiving the user input may be omitted. For example, when it is determined that the surrounding environment of the wearable device 110 is not quiet, the wearable device 110 may recommend noise cancellation to be turned on, or may turn on noise cancellation without receiving an input of the user 130 with respect to the recommendation. A condition where the wearable device 110 recommends noise cancellation to be turned on, or turns on noise cancellation without receiving an input of the user 130 with respect to the recommendation may be previously set and stored on the wearable device 110.

According to an embodiment, when the surrounding environment of the wearable device 110 is quiet, the wearable device 110 may recommend noise cancellation to be turned off (operation 1715). For example, because the surrounding environment of the wearable device 110 is quiet, the wearable device 110 may provide a message suggesting an on-going noise cancellation function to be turned off, to the wearable device 110 or the user terminal 120. According to an embodiment, the message suggesting noise cancellation to be turned off may be provided in a pop-up window form on the wearable device 110 or the user terminal 120. The pop-up window may include a phrase regarding noise cancellation turn off recommendation such as "Will you turn off noise cancellation?". The pop-up window may also include a first button (e.g., yes) and a second button (e.g., no) enabling the user 130 to select whether to turn off noise cancellation. According to an embodiment, the message may be output in an audio message form by the wearable device 110, and thus, may be provided to the user 130. However, embodiments of the disclosure are not limited thereto. According to an embodiment, user preference information 1702-1 provided by the DB 408 may be used when the wearable device 110 recommends noise cancellation to be turned on. For example, even when the surrounding environment of the wearable device 110 is quiet, when the user preference information 1702-1 represents that the user 130 prefers continuous use of the noise cancellation function, the wearable device 110 may not recommend noise cancellation to be turned off.

The wearable device 110 may receive a user input (operation 1735). For example, the wearable device 110 receive an input of the user 130 regarding turn-off recommendation of noise cancellation, through the wearable device 110 or the user terminal 120. For example, when the user 130 wants to turn off noise cancellation, the user 130 may provide a user input by touching or clicking the first button representing that noise cancellation is turned off. When the user 130 does not want to turn off noise cancellation, the user 130 may provide a user input by touching or clicking the second button representing that noise cancellation is not turned off. According to an embodiment, the wearable device 110 may store, in the DB 408, environment information 1704 indicating a current surrounding environment of the wearable device 110. According to an embodiment, the environment information 1704 stored in the DB 408 may be used to generate the user preference information 1702-1 or the user preference information 1702-2 during recommendation of noise cancellation.

The wearable device 110 may turn off noise cancellation (operation 1740). For example, when the user 130 selects noise cancellation to be turned off, through a user input, the wearable device 110 may turn off a noise cancellation function of the wearable device 110. According to an embodiment, operation 1715 of recommending noise cancellation to be turned off and operation 1735 of receiving the user input may be omitted. For example, when it is determined that the surrounding environment of the wearable device 110 is quiet, the wearable device 110 may recommend noise cancellation to be turned off, or may turn off noise cancellation without receiving an input of the user 130 with respect to the recommendation. A condition where the wearable device 110 recommends noise cancellation to be turned off, or turns off noise cancellation without receiving an input of the user 130 with respect to the recommendation may be previously set and stored on the wearable device 110. As shown in FIG. 17, the wearable device 110 may analyze the surrounding environment of the wearable device 110 and change an operation according to a result of the analysis, thereby reducing power consumption of the wearable device 110 due to the noise cancellation function.

An embodiment of the disclosure may also be implemented in the form of a recording medium including instructions executable by a computer, such as a program module executed by a computer. Computer-readable media may be any available media accessible by a computer and includes both volatile and nonvolatile media and removable and non-removable media. Computer-readable media may also include computer storage media and communication media. Computer storage media includes both volatile and nonvolatile, removable and non-removable media implemented in any method or technology for storage of information such as computer readable instructions, data structures, program modules or other data. Communication media may typically include computer readable instructions, data structures, or other data in a modulated data signal, such as program modules.

Terms "unit" and "module" used herein may be a hardware component such as a processor or circuit, and/or a software component executed by a hardware component such as a processor.

"Unit" and "module" may be stored in an addressable storage medium and may be implemented by a program that can be executed by a processor. For example, "unit" and "module" may be implemented by components (such as, software components, object-oriented software components, class components, and task components) and processes, functions, properties, procedures, sub-routines, segments of a program code, drivers, firmware, a microcode, circuitry, data, database, data structures, tables, arrays, and variables.

The particular executions described herein are merely an embodiment and do not limit the scope of the disclosure concept in any way. For the sake of brevity, conventional electronics, control systems, software development and other functional aspects of the systems may not be described in detail.

An expression "including at least one of a, b, or c" used herein means "including only a", "including only b", "including only c", "including a and b", "including b and c", "including a and c", or "including both a, b and c".

While the disclosure has been particularly shown and described with reference to exemplary embodiments thereof, it will be understood that various changes in form and details may be made therein without departing from the spirit and scope of the disclosure. Thus, the above-described embodiments should be considered in descriptive sense only and not for purposes of limitation. For example, each component described as a single type may be implemented in a distributed manner, and similarly, components described as being distributed may be implemented in a combined form.

The scope of the disclosure is indicated by the scope of the claims to be described later rather than the above detailed description, and all changes or modified forms derived from the meaning and scope of the claims and the concept of equivalents thereof should be interpreted as being included in the scope of the disclosure.

What is claimed is:

1. A method of operating a wearable device, the method comprising:
   receiving, as an input, a surrounding sound of the wearable device;
   determining an operation mode from among a plurality of operation modes, based on the received input; and
   performing a preset operation according to the determined operation mode,
   wherein the plurality of operation modes comprise a conversation mode representing a conversation state between a user of the wearable device and a speaker,
   wherein the determining the operation mode from among the plurality of operation modes comprises determining the conversation mode to be the operation mode of the wearable device, based on determining that a voice signature detected from the received input matches with a pre-stored voice signature of a plurality of pre-stored voice signatures, wherein, based on the determining that the detected voice signature matches with the pre-stored voice signature, the preset operation comprises:

canceling noise from the received input, adjusting a volume of an audio of a content reproduced by the wearable device, and amplifying a voice of the speaker, wherein the plurality of operation modes further comprise: a power control mode for controlling power consumption of the wearable device, and wherein, based on determining the power control mode to be the operation mode of the wearable device, the preset operation further comprises:

adjusting a sampling rate of the input; and deactivating noise cancellation.

2. The method of claim 1, wherein the plurality of operation modes further comprise an announcement mode representing for a detection of an announcement from an external sound source.

3. The method of claim 2, wherein the determining the operation mode from among the plurality of operation modes comprises determining the announcement mode to be the operation mode of the wearable device, based on determining that an announcement signature is detected from the received input.

4. The method of claim 2, wherein the determining the operation mode from among the plurality of operation modes comprises determining the power control mode to be the operation mode of the wearable device, based on determining that a magnitude of the received input is less than a threshold.

5. The method of claim 2, wherein, based on determining the announcement mode to be the operation mode of the wearable device, the preset operation comprises at least one of:

canceling the noise from the received input; and adjusting the volume of the audio of the content reproduced by the wearable device.

6. The method of claim 1, wherein the preset operation further comprises, based on the determining that the detected voice signature matches with the pre-stored voice signature, updating the pre-stored voice signature based on the detected voice signature.

7. The method of claim 1, further comprising:

sensing brainwaves of the user of the wearable device;

identifying a sleep state of the user by analyzing the sensed brainwaves; and performing noise cancellation, based on the identified sleep state.

8. A wearable device comprising:

a memory configured to store one or more instructions; and at least one processor operatively connected to the memory and configured to execute the one or more instructions to:

receive, as an input, a surrounding sound of the wearable device;

determine an operation mode from among a plurality of operation modes, based on the received input; and perform a preset operation according to the determined operation mode, wherein the plurality of operation modes comprise a conversation mode representing a conversation state between a user of the wearable device and a speaker, wherein the determining the operation mode from among the plurality of operation modes comprises determining the conversation mode to be the operation mode of the wearable device, based on determining that a voice signature detected from the received input matches with a pre-stored voice signature of a plurality of pre-stored voice signatures, wherein, based on the determining that the detected voice signature matches with the pre-stored voice signature, the preset operation comprises:

canceling noise from the received input, adjusting a volume of an audio of a content reproduced by the wearable device, and amplifying a voice of the speaker, wherein the plurality of operation modes further comprise a power control mode for controlling power consumption of the wearable device, and wherein, based on determining the power control mode to be the operation mode of the wearable device, the preset operation further comprises:

adjusting a sampling rate of the input; and deactivating noise cancellation.

9. The wearable device of claim 8, wherein the plurality of operation modes further comprise an announcement mode representing for a detection of an announcement from an external sound source.

10. The wearable device of claim 9, wherein the at least one processor is configured to execute the one or more instructions to determine the announcement mode to be the operation mode of the wearable device, based on determining that an announcement signature is detected from the received input.

11. The wearable device of claim 9, wherein the at least one processor is configured to execute the one or more instructions to determine the power control mode to be the operation mode of the wearable device, based on determining that a magnitude of the received input is less than a threshold.

12. The wearable device of claim 9, wherein, based on determining the announcement mode to be the operation mode of the wearable device, the preset operation comprises at least one of:

canceling the noise from the received input; and adjusting the volume of the audio of the content reproduced by the wearable device.

13. The wearable device of claim 8, wherein the preset operation comprises, based on the determining that the detected voice signature matches with the pre-stored voice signature, updating the pre-stored voice signature based on the detected voice signature.

* * * * *